US006682739B1

(12) United States Patent
Greene et al.

(10) Patent No.: US 6,682,739 B1
(45) Date of Patent: Jan. 27, 2004

(54) METHODS OF INHIBITING OSTEOCLASTOGENESIS

(75) Inventors: Mark I. Greene, Penn Valley, PA (US); Ramachandran Murali, Drexel Hill, PA (US); Kazuhiro Aoki, Narashino (JP); William Carle Horne, Branford, CT (US); Roland Baron, Guilford, CT (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/627,775

(22) Filed: Jul. 28, 2000

Related U.S. Application Data
(60) Provisional application No. 60/146,090, filed on Jul. 28, 1999.

(51) Int. Cl.$^7$ ...................... A61K 39/00; A61K 39/395; A61K 45/00; A01N 37/18; C07K 1/00
(52) U.S. Cl. ................ 424/185.1; 424/85.1; 424/184.1; 424/192.1; 424/178.1; 514/12; 514/2; 514/8; 514/885; 530/350; 530/351
(58) Field of Search ........................... 424/185.1, 178.1, 424/184.1, 192.1, 85.1; 514/12, 2, 8, 885; 530/350, 351, 300; 435/69.2, 69.1

(56) References Cited

U.S. PATENT DOCUMENTS

| 4,215,051 A |  | 7/1980 | Schroeder et al. ........ 260/346.7 |
|---|---|---|---|
| 4,946,778 A |  | 8/1990 | Ladner et al. .............. 435/69.6 |
| 5,470,952 A | * | 11/1995 | Stahl et al. .................. 530/350 |
| 5,849,865 A | * | 12/1998 | Cheng et al. ................ 530/317 |

FOREIGN PATENT DOCUMENTS

| EP |  | 0 045 665 | 2/1982 |  |
|---|---|---|---|---|
| WO |  | WO-9853842 A1 | * 12/1998 | .......... A61K/38/00 |

OTHER PUBLICATIONS

Kwon et al., "TR1, a new member of the tumor necrosis factor receptor superfamily, induces fibroblast proliferation and inhibits osteoclastogenesis and bone resorption", The Faseb Journal, (1998), vol. 12, pp. 845–854.*
Yamaguchi et al."Characterization of structural domains of human osteoclastogenesis inhibitory factor", J. Biological Chemistry, 1998, 273(9), 5117–23.*
Takasaki et al. "Structure–based design and characterization of exocyclic peptidomimetics that inhibit TNF–alfa binding to its receptor",Nature Biotechnology, 1997, 15, 1266–70.*
Kitazawa et al."Interleukin–1 receptor antagonist and tumor necrosis factor binding protein decrease osteoclast formation and bone resorption in ovariectomized mice," J.Clin. Invest., 1994, 94, 2397–2406.*
Wong et al.,"Trance is a TNF family member that regulates dendritic cell and osteoclast function," J. Leukocyte Biology, vol. 65, 1999, 715–724.*

U.S. provisional application Ser. No. 60/146,090, filed Jul. 28, 1999, Greene et al.
Kitazawa, R., et al., "Interleukin–1 receptor antagonist and tumor necrosis factor binding protein decrease osteoclast formation and bone resorption in ovariectomized mice," J. clin. Invest., 1994, 94, 2397–2406.
Yamaguchi, K., et al., "Characterization of structural domains of human osteoclastogenesis inhibitory factor," J. Biological Chemistry, 1998, 273(9), 5117–5123.
Ahmed, A.K., et al., "Nonenzymic reactivation of reduced bovine pancreatic ribonuclease by air oxidation and by glutathione oxidoreduction buffers," J. Biological Chem., 1975, 250(21), 8477–8482.
Albericio, F., et al., "Improved approach for anchoring $N^\alpha$–9–fluorenylmethyloxycarbonylamino acids as p–alkoxybenzyl esters in solid–phase peptide synthesis," Int. J. Peptide protein Res., 1985, 26, 92–97.
Anderson, D.M., et al., "A homologue of the TNF receptor and its ligand enhance T–cell growth and dendritic–cell function," Nature, 1997, 390, 175–179.
Ausubel, et al. (eds.), "Current protocalls in molecular biology," Molecular Biology, 1987, vol. 2, Greene Publish. Assoc. & Wiley Interscience.
Ausubel, et al., Current protocols in Molecular Biology, Greene Publishing Associates & Wiley Interscience, NY, 1989.
Banner, D.W., et al., "Crystal structure of the soluble human 55 kd TNF receptor–human TNFβ complex: implications for TNF receptor activation," Cell, 1993, 73, 431–445.
Beutler, B., et al., "Unraveling function in the TNF ligand and receptor families," Science, 1994, 264, 667–668.
Beutler, B., et al., "An evolutionary and functional approach to the TNF receptor/ligand family," Microbial Pathogenesis and Immune Response, Ann. NY Acad. Sci., 1994, 118–133.
Brisson, N., et al., "Expression of a bacterial gene in plants by using a viral vector," Nature, 1984, 310, 511–514.
Broglie, R., et al., "Light–regulated expression of a pea ribulose–1,5–bisphosphate carboxylase small subunit gene in transformed plant cells," Science, 1984, 224, 838–843.

(List continued on next page.)

Primary Examiner—Gary Benzion
Assistant Examiner—Arun Kr. Chakrabarti
(74) Attorney, Agent, or Firm—Darby & Darby

(57) ABSTRACT

Methods of inhibiting osteoclastogenesis and the activity of osteoclasts are disclosed. Methods of treating patients who have diseases characterized bone loss are disclosed. The present invention also provides peptides and peptide analogues designed from a binding loop of a member of the tumor necrosis factor receptor (TNF-R) superfamily. According to the methods, an amount of an inhibitor effective to inhibit osteoclastogenesis is administered to the patient. Methods of modulating dendritic cell maturation, T cell proliferation, and/or CD40 receptor systems in an individual are disclosed. The methods comprise the step of administering to the individual an amount of an inhibitor effective to modulating dendritic cell maturation, T cell proliferation, and/or CD40 receptor systems.

41 Claims, 1 Drawing Sheet

OTHER PUBLICATIONS

Cole, S.P.C., et al., "The EBV–hybridoma technique and its application to human lung cancer," *Monoclonal Antibodies and Cancer Therapy*, 1985, Reisfeld, R.A, et al. (eds.), Alan R. Liss, Inc., 77–96.

Coruzzi, G., et al., "Tissue–specific and light–regulated expression of a pea nuclear gene encoding the small subunit of ribulose–1,5–bisphosphate carboxylase," *EMBO J.*, 1984, 3(8), 1671–1679.

Cote, R.J., et al., "Generation of human monoclonal antibodies reactive with cellular antigens," *Proc. Natl. Acad. Sci., USA*, 1983, 80, 2026–2030.

Döring, E., et al., "Identification and characterization of a TNFα antagonist derived from a monoclonal antibody," *Molecular Immunol.*, 1994, 31(14), 1059–1067.

Fasman, CRC Practical Handbook of Biochemistry and Molecular Biology, *CRC Press, Inc.*, 1989.

Filvaroff, E., et al., "Bone remodelling: A signalling system for osteoclast regulation," *Curr. Biol.*, 1998, 8, R679–R682.

Fingl, E., et al., "General Principles," In: The Pharmacological Basis of Therapeutics, 1975, Chapter 1, 1–46.

Giralt, et al. (eds.), *ESCOM*, 1991 Leiden, The Netherlands.

Green and Wuts, *John Wiley & Sons, New York*, $2^{nd}$ ed., 1991.

Grierson, D., et al., "Genetic transformation of plants by agrobacterium," *Plant Molecular Biology*, $2^{nd}$ Ed., Blackie, London, 1988, Chapters 7–9, 141–211.

Gruss, H., et al., "The TNF ligand superfamily and its relevance for human diseases," *Cytokines and Mol. Ther.*, 1995, 1, 75–105.

Gurley, W.B., et al., "Upstream sequences required for efficient expression of a soybean heat shock gene," *Mol. Cell. Biol.*, 1986, 559–565.

Habeeb, A.F.S.A., "A sensitive method for localization of disulfide containing peptides in column effluents," *Anal. Bioch.*, 1973, 56, 60–65.

Hann, M.M., et al., "On the double bond isostere of the peptide bond: preparation of an enkephalin analogue," *J. Chem. Soc. Perkin Trans., I*, 1982, 307–314.

Holladay, M.W., et al., "Synthesis of hydroxyethylene and ketomethylene dipeptide isosteries," *Tetrahedron Lett.*, 1983, 24(41), 4401–4404.

Hruby, V.J., "Conformational restrictions of biologically active peptides via amino acid side chain groups," *Life Sci.*, 1982, 31, 189–199.

Hudson, D., et al., "Methionine enkephalin and isosteric analogues," *Int. J. Prot. Res.*, 1979, 14, 177–185.

Huse, et al., "Generation of a large combinatorial library of the immunoglobulin repertoire in phage lambda," *Science*, 1989, 246, 1275–1281.

Jennings–White, C., et al., "Synthesis of ketomethylene analogs of dipeptides," *Tetrahedron Lett.*, 1982 23(25), 2533–2534.

Kamber, B., et al., "96. The synthesis of cystine peptides by iodine oxidation of S–Trityl–cysteine and S–Acetamidomethyl–cysteine peptides," *Helv Chim Acta*, 1980, 63(Fasc. 4), 899–915.

Köhler, G., et al., "Continuous cultures of fused cells secreting antibody of predefined specificity," *Nature*, 1975, 256, 495–497.

Kong, Y., et al., "Osteoprotegerin ligand: A common link between osteoclastogenesis, lymph node formation and lymphocyte development," *Immunol. And Cell Biology*, 1999, 77, 188–193.

Kozbor, D., et al., "The production of monoclonal antibodies from human lymphocytes," *Immunology Today*, 1983, 4(3), 72–79.

Livingstone, D.M., 91. Immunoaffinity chromatography of proteins, *Methods in Enzymology*, Affinity Techniques, Academic Press, 1974, 723–731.

Logan, J., et al., "Adenovirus tripartite leader sequence enhances translation of mRNAs late after infection," *Proc. Natl. Acad. Sci. USA*, 1984, 81, 3655–3659.

Mackett, M., et al., Vaccinia virus: A selectable eukaryotic cloning and expression *Proc. Natl. Acad. Sci. USA*, 1982, 79, 7415–7419.

Mackett, M., et al., "General method for production and selection of infectious vaccinia virus recombinants expressing foreign genes," *J. Virol.*, 1984, 49(3), 857–864.

Maniatis, et al., Molecular Cloning A Laboratory Manual, Cold Spring Harbor Laboratory, NY, 1989.

Moore, W.T., et al., "Mass spectrometric analyses of the activation products of the third component of complement," In Techniques in Protein Chemistry VII, Marsak (ed.), Academic press, San Diego, CA, 1996, 81–91.

Morley, J.S., "Modulation of the action of regulatory peptides by structural modification," *Trends Pharm. Sci.*, 1980, 463–468.

Morrison, S.L., et al., "Chimeric human antibody molecules: mouse antigen–binding domains with human constant region domains," *Proc. Natl. Acad. Sci., USA*, 1984, 81, 6851–6855.

Neuberger, M.S., et al., "Recombinant antibodies possessing novel effector functions," *Nature*, 1984, 312, 604–608.

Nicholson, G.C., et al., "Abundant calcitonic receptors in isolated rat osteoclasts," *J. Clin. Invest.*, 1986, 78, 355–360.

Panicali, D., et al., "Construction of poxviruses as cloning vectors: Insertion of the thymidine kinase gene from herpes simplex virus into the DNA of infectious vaccinia virus," *Proc. Natl. Acad. Sci.*, 1982, 79, 4927–4931.

Peppel, K., et al., "A tumor necrosis factor (TNF) receptor–IgG heavy chain chimeric protein as a bivalent antagonist of TNF activity," *J. Exp. Med.*, 1991, 174, 1483–1489.

Ponder, J.W., et al., "Tertiary templates for proteins use of packing criteria in the enumeration of allowed sequences for different structural classes," *J. Mol. Biol.*, 1987, 193, 775–791.

Scopes, Protein Purification: Principles and Practice, 1984, Spriger–Verlag New York, Inc., NY.

Smith, G.E., et al., "Molecular engineering of the *Autographa californica* nuclear polyhedrosis virus genome: deletion mutations within the polyhedrin gene," *J. Virol.*, 1983, 46, 584–593.

Spatola, A.F., "Peptide backbone modifications: A structure–activity analysis of peptides containing amide bond surrogates. Conformational constraints, and rela," In: Chemistry and Biochemistry of Amino Acids peptides and proteins, Weinstein (ed.), *Marcel Dekker, New York*, 1983, p. 267–357.

Spatola, A.F., et al., "Structure–activity relationships of enkephalins containing serially replaced thiomethylene amide bond surrogates," *Life Sci.*, 1986, 38, 1243–1249.

Stewart, et al., Solid Phase peptide Synthesis, 2d ed., *Pierce Chemical Company*, Rockford, IL, 1984.

Suda, T., et al., "Modulation of osteoclast differentiation and function by the new members of the tumor necrosis factor receptor and ligand families," *Endocrine Reviews*, 1999, 20(3), 345–357.

Takamatsu, N., et al., "Expression of bacterial chloramphenicol acetyltransferase gene in tobacco plants mediated by TMV–RNA," *EMBO J.*, 1987, 6(2), 307–311.

Takasaki, W., et al., "Structure–based design and characterization of exocyclic peptidominetics that inhibit TNFα binding to its receptor," *Nature Biotechnology*, 1997, 15, 1266–1270.

Takeda, S., et al., "Construction of chimaeric processed immunoglobulin genes containing mouse variable and human constant region sequences," *Nature*, 1985, 314, 452–454.

Tam, J.P., et al., "Improved synthesis of 4–(boc–aminoacyloxymethyl)–phenylacetic acids for use in solid phase peptide synthesis," *Synthesis*, 1979, 955–957.

Weissbach, et al., "[26]Gene transfer in plants: production of transformed plants using Ti plasmid vectors" "[27] Plant virus vectors: cauliflower mosaic virus," "[28] Direct gene transfer to plants," Methods for Plant Molecular Biology, Academic Press, NY, *Section VIII*, 1988, 421–463.

Williams, R.O., et al., "Successful therapy of collagen–induced arthritis with TNF receptor–IgG fusion protein and combination with anti–CD4," *Immunol.*, 1995, 84, 433–439.

Wong, B., et al., "Trance is a TNF family member that regulates dendritic cell and osteoclast function," *J. Leukocyte Biol.*, 1999, 65, 715–724.

Zhang, X., et al., "Synthetic CD4 exocyclic peptides antagonize CD4 holoreceptor binding and T cell activation," *Nature Biotech.*, 1996, 14, 472–475.

Zhang, X., et al., "Synthetic CD4 exocyclics inhibit binding of human immunodeficiency virus type 1 envelope to CD4 and virus replication in T lymphocytes," *Nature Biotech.*, 1997, 15, 150–154.

Bucay, N., et al., "osteoprotegerin–deficient mice develop early onset osteoporosis and arterial calcification," *Genes Dev.*, May 1, 1998, 12(9), 1260–1268.

Kong, Y., et al., "OPGL is a key regulator of osteoclastogenesis, lymphocyte development and lymph–node organogenesis," *Nature*, Jan. 28, 1999, 397, 315–323.

Lacey, D.L., "Osteoprotegerin ligand is a cytokine that regulates osteoclast differentiation and activation," *Cell*, Apr. 17, 1998, 93(2), 165–176.

McOsker, J.E., et al., "Preclinical pharmacology of risedronate, a third generation bisphosphonate," *J. Bone & Mineral Research*, ISSN: 0884–0431, Aug. 28–31, 1990, p. S105, No. 128, Abstract.

Mortensen, L., et al., "Risedronate increases bone mass in an early postmenopausal population: two years of treatment plus one year of follow–up," *J. Clinical Endocrinology and Metabolism*, Feb. 1998, 83(2), 396–402.

Shalhoub, V., et al., "Osteoprotegerin and osteoprotegerin ligand effects on osteoclast formation from human peripheral blood mononuclear cell precursors," *J. Cellular Biochem.*, Feb. 1, 1999, 72(2), 251–261.

Sietsema, W.K., et al., "Antiresorptive dose–responserelationships across three generations of bisphosphonates," *Drugs Exptl. Clin. Res.*, 1989, XV(9), 389–396.

Simonet, W.S., et al., "Osteoprotegerin: a novel secreted protein involved in the regulation of bone density," *Cell*, Apr. 18, 1997, 89(2), 309–319.

Singer, F.R., et al., "Risedronate, a highly effective oral agent in the treatment of patients with severe paget's disease," *J. Clinical Endocrinology and Metabolism*, Jun. 1998, 83(6), 1906–1910.

Siris, E.S., et al., "Risedronate in the treatment of paget's disease of bone: an open label, multicenter study," *J. Bone and Mineral Research*, Jun. 6, 1998, 13(6), 1032–1038.

Van Beek, E., "Dissociation of binding and antiresorpive properties of hydroxybisphosphonates by substitution of the hydroxyl with an amino group," *J. Bone and Mineral Research*, 1996, 11(10), 1492–1497.

Frattini, A. et al., "Defects in TCIRG1 subunit of the vacuolar proton pump are responsible for a subset of human autosomal recessive osteopetrosis", *Nature Genetics*, 1999, 23, 447–451.

Kornak, U. et al., "Loss of the CIC–7 chloride channel leads to osteopetrosis in mice and man", *Cell*, 2001, 104, 205–215.

Lacey, D.L. et al., "Osteoprotegerin ligand modulates murine osteoclast survival in vitro and in vivo", *Am. Jrl. Of Pathology*, 2000, 157(2), 435–448.

Li, Y.P. et al., "Atp6i–deficient mice exhibit severe osteopetrosis due to loss of osteoclast–mediated extracellular acidfication", *Nature Genetics*, 1999, 23, 447–451.

Li, J. et al., "RANK is the intrinsic hematopoietic cell surface receptor that controls osteoclastogenesis and regulation of bone mass and calcium metabolism", *PNAS*, 2000, 97(4), 1566–1571.

Scimeca, J.C., "The gene encoding the mouse homologue of the human osteoclast–specific 116–kDa V–ATPase subunit bears a deletion in osteosclerotic (oc/oc) mutants", *Bone*, 2000, 26(3), 207–213.

Shalhoub, V. et al., "Characterization of osteoclast precursors in human blood", *British Jrl. Of Haematology*, 2000, 111, 501–512.

Weitzmann, M.N. et al., "T cell activation induces human osteeoclast formation via receptor activator of nuclear factor k B ligand–dependent and –Independent mechanisms", *Jrl. of Bone and Mineral Research*, 2001, 16(2), 328–337.

\* cited by examiner

|  | 70 | 80 | 90 | 100 | 110 | 120 | 130 | 140 |
|---|---|---|---|---|---|---|---|---|
| TNF-R p55 | | DCRECESGSFTASENHLRHCLSCSK.. | CRKEMGQVEISS | CTVDRDTV | CGCRKNQYRHYWSENLFQ. | C | FN CSLC LNG... | T |
| TNF-R p75 | VCDSCEDSTYTQLWNWVPECLSCGSRC | SSDQVE...TQA | CTREQNRI | CTCRPGWYCALSKQEGCRL | C | AP LRKC RPGFGV | A |
| TNF-R-rp | VCATCAENSYNEHWNYL..TICQLCRP | CDPVMGLEEIAP | CTSKRKTQ | CRCQPGMFCAAWALE.CTH | C | EL LSDC PPGTEA | E |
| NGF-R p75 | .CEPCLDSVTFSDVVSATEPCKPCTEC | VGLQSMSAP... | CVEADDAV | CRCAYGYYQDETTGRCEAC | R | VC EAGS GLVFSC | Q |
| CD27 | QCDPCIPGVSFS...PDHHTRPHCESC | RHCNSGLLVRN. | CTITANAE | CACRNGW......... | | ........QC | R |
| CD30(proximal) | CRKQCEPDYYLDEADRCTACVTCSRD. | .....DLVEKTP | CAWNSSRV | CECRPGMFCSTSAVNSCAR | C | FF HSVC PAGMIV | K |
| CD30(distal) | CRKQCEPDYYLDEAGRCTACVSCSRD. | .....DLVEKTP | CAWNSSRT | CECRPGMICATSATNSCAR | C | VP YPIC AAETVT | K |
| CD40 | ECLPCGESEFLDTWNR..ETHCHQHKY | CDPNLGLRVQQK | GTSETDTI | CTCEEGWHCT...SEACES | C | VL HRSC SPGFGV | K |
| Fas | DCVPCQEGKEYTDKAHF.....SSK.. | CRR......... | | ............ | | ..CRLC DEGHGL | E |
| OX40 | .CRPC.GPGFYNDVVSS.KPCKPCTWC | .NLRSGSERKQL | CTATQDTV | CR............ | | ..CRAGT QPLDSY | . |
| 4-1BB | .CSPCPPNSF.....SSAGGQRTCDIC | RQCKGVFRTRKE | CSSTSNAE | CDCTPGFH..... | | CLGAGC S MC EQDCKQGQEL | T |

Figure 1

METHODS OF INHIBITING OSTEOCLASTOGENESIS

CROSS-REFERENCE TO RELATED APPLICATIONS

The present application U.S. application Ser. No. 60/146,090, filed Jul. 28, 1999, which is hereby incorporated by reference in its entirety.

ACKNOWLEDGMENT OF GOVERNMENT RIGHTS

The present invention was made under Grant EY09332 from the National Institutes of Health. The Government may have certain rights to the invention.

FIELD OF THE INVENTION

The present invention relates to the methods of down-modulating osteoclastogenesis activity, thereby inhibiting bone matrix erosion and thus preventing bone loss and treating bone diseases. The present invention also relates to peptides and peptide analogues which inhibit TNF binding to its cellular receptors, methods of designing similar peptides and peptide analogues, and methods of using such compounds to inhibit the biological activities of TNF particularly those activities relating to bone resorption, thereby antagonizing its undesirable clinical effects.

BACKGROUND OF THE INVENTION

Osteoclasts are large multinuclear cells which function to erode bone matrix. They are related to macrophage and other cells that develop from monocyte cells. Like macrophage, osteoclasts are derived from haematopoietic progenitor cells.

Bone matrix erosion is a normal process which occurs in coordination with bone matrix formation, a process in which osteoblasts are involved. Essentially, osteoblasts erode bone matrix and tunnel into bone while osteoblasts follow, line the walls of the tunnel and form new bone matrix. Typically, in a normal adult, about 5–10% of bone is replaced by these processes annually.

Bone diseases such as osteoporosis and Paget's disease are characterized by a loss of bone. Similarly, metastatic bone disease, rheumatoid arthritis, and periodontal bone disease are also characterized by bone loss. In many cases, bone loss leads to fractures in patients. In addition to pain and suffering, patients become physically impaired which often leads to complications having negative consequences on patient health and quality of life. Moreover, the economic costs attributable to these diseases are tremendous.

Receptors and ligands of the Tumor Necrosis Factor (TNF) family have recently been shown to play an essential part in the differentiation and activity of osteoclasts and therefore play a role in bone resorption. On the one hand, TNF-α is known to promote osteoclastogenesis, the generation of osteoclasts. On the other hand, a TNF-like molecule present on and/or secreted by osteoclasts and stromal cells, referred to interchangeably in the field and herein as "Receptor activator of NF-κB ligand", (RANKL), "Osteoclast differentiation factor" (ODF), "Osteoprotegerin ligand" (OPGL), and "TNF-related activation-induced cytokine" (TRANCE), interacts with a TNF-receptor-like molecule, referred to in the field and herein as "Receptor activator of NF-κB ligand", (RANK), which, present in the membranes of osteoclast precursors and mature osteoclasts, regulates osteoclastogenesis and the resorbing activity of mature osteoclasts. The utilization of TNF-α antagonists, such as a monoclonal antibodies, for therapeutic purposes, has proven difficult, however, because of immunity to the large molecule, and limited entry into some specialized compartments of the body. Suda, et al. (Endocrine Reviews 20(3):345–357, 1999), which is incorporated herein by reference, describe osteoclast differentiation and function. Filvaroff, E and R. Derynck (Curr. Biol. 8:R679–R682, 1998) which is incorporated herein by reference, refer to bone remodeling and a signaling system for osteoclast regulation.

Thus, there is a need for methods of regulating osteoclastogenesis and the resorbing activity of mature osteoclasts. There is also a need for methods of preventing bone loss and treating bone diseases.

SUMMARY OF THE INVENTION

The present invention relates to methods of inhibiting osteoclastogenesis and the resorbing activity of mature osteoclasts. According to the present invention, an amount of a TRANCE/RANK inhibitor effective to inhibit osteoclast bone erosion activity is administered to a patient.

The present invention relates to methods of treating patients who have diseases characterized by bone loss. According to the present invention, an amount of a TRANCE/RANK inhibitor effective to inhibit osteoclastogenesis is administered to a patient.

The present invention relates to pharmaceutical compositions which comprise a TRANCE/RANK inhibitor in an amount effective to inhibit osteoclastogenesis.

The present invention relates to methods of modulating dendritic cell maturation, T cell proliferation, and/or CD40 receptor systems in an individual comprising the step of administering to the individual an amount of a TRANCE/RANK inhibitor effective to modulate dendritic cell maturation, T cell proliferation, and/or CD40 receptor systems.

The present invention relates to the use of peptides and peptide analogues designed from a binding loop of a TNF-R superfamily member. In particular, it relates to the use of peptides and peptide analogues designed from three binding loops of TNF-R. More specifically, the invention relates to peptides and peptide analogues which inhibit activities relating to bone resorption.

Generally, compounds used in the present invention are cyclic peptides or peptide analogues which are modified at their termini with hydrophobic moieties. In embodiments wherein the compound is a peptide, the peptide corresponds in primary sequence to a binding loop of a member of the TNF-R superfamily or a portion thereof. In a preferred embodiment, the peptide used in the invention corresponds in primary sequence to a binding loop of TNF-R p55 or a portion thereof. In certain embodiments, one or more amino acid residues within the peptide are substituted with other amino acid residues. Typically, such amino acid substitutions are conservative, i.e.,the amino acid residues are replaced with other amino acid residues having similar physical and/or chemical properties. In embodiments wherein the compound is a peptide analogues, the analogues is obtained by replacing at least one amide linkage in the peptide with a substituted amide or an isostere of amide.

In an illustrative embodiment, a compound used in the invention has the following formula:

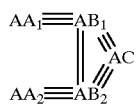

(I)

wherein:

AC is a peptide of 3–18 amino acid residues which corresponds in primary sequence to a binding loop of a TNF-R superfamily member, and which may optionally contain one or more conservative amino acid substitutions, or an analogue thereof wherein at least one amide linkage is replaced with a substituted amide or an isostere of amide;

$AB_1$ is a moiety having a first functional group capable of forming a covalent linkage with one terminus of AC, a second functional group capable of forming a covalent linkage with $AB_2$ and a third functional group capable of forming a covalent linkage with $AA_1$;

$AB_2$ is a moiety having a first functional group capable of forming a covalent linkage with the second terminus of AC, a second functional group capable of forming a covalent linkage with $AB_1$ and a third functional group capable of forming a covalent linkage with $AA_2$;

$AA_1$ is a moiety having hydrophobic properties and a functional group capable of forming a covalent linkage with the third functional group of $AB_1$;

$AA_2$ is a moiety having hydrophobic properties and a functional group capable of forming a covalent linkage with the third functional group of $AB_2$;

"═" is a covalent linkage; and

"≡" is a covalent linkage.

In a preferred embodiment of the compounds of formula (I), AC is a peptide which corresponds in primary sequence to a binding loop of TNF-R p55 and which optionally may contain one or more conservative amino acid substitutions, or an analogue thereof. In a particularly preferred embodiment, the peptides and peptide analogues specifically inhibit osteoclastogenesis.

BRIEF DESCRIPTION OF THE DRAWINGS

FIG. 1 depicts the sequence alignment of amino acids in certain extracellular Cys-rich domains of TNF-R superfamily members: TNF-R p55 (SEQ ID NO:1), TNF-R p 75 (SEQ ID NO:2), TNF-R-rp (SEQ ID NO: 3), NGF-R p75 (SEQ ID NO: 4), CD27 (SEQ ID NO:5), CD30 (proximal) SEQ ID NO:6), CD30 (distal) (SEQ ID NO:7), CD40 (SEQ ID NO:10), and 4-1BB (SEQ ID NO:11).

DETAILED DESCRIPTION OF PREFERRED EMBODIMENTS

The invention provides methods for treating individuals that have diseases characterized by bone loss. TRANCE/RANK inhibitors are administered to the individual in an amount effective to inhibit osteoclastogenesis and/or osteoclast function and thereby reduce bone loss, i.e. a therapeutically effective amount.

The invention also provides novel therapeutic pharmaceutical compositions for treating diseases characterized by bone loss. The pharmaceutical compositions comprise a therapeutically effective amount of TRANCE/RANK inhibitors and a pharmaceutically acceptable carrier or diluent. In preferred embodiments, the pharmaceutical compositions are injectable pharmaceutical compositions, i.e. they are sterile, pyrogen-free, free of particulate matter, essentially isotonic, and are otherwise suitable for injection into humans.

As used herein, the term "TRANCE/RANK inhibitors" refers to peptides and peptide analogues which inhibit osteoclastogenesis and/or osteoclast function. TRANCE/RANK inhibitors can function as an antagonist of the cellular receptor RANK by inhibiting TRANCE/RANK.

As used herein, the term "diseases characterized by bone loss" is meant to refer to diseases, conditions, disorders and syndromes which have as a symptom or pathology a decrease in bone mass or density. Examples of diseases characterized by bone loss include, but are not limited to, osteoporosis, Paget's disease, metastatic bone disease, rheumatoid arthritis and periodontal bone disease.

As used herein, the term "bone resorption" refers to the undesired loss of bone caused at least in part by osteoclast activity.

As used herein, the term "therapeutically effective amount" is meant to refer to an amount of a compound which produces a medicinal effect observed as reduction in the rate of bone loss in an individual when a therapeutically effective amount of a compound is administered to an individual who is susceptible to or suffering from a disease characterized by bone loss. Therapeutically effective amounts are typically determined by the effect they have compared to the effect observed when a composition which includes no active ingredient (i.e. a control) is administered to a similarly situated individual.

As used herein, the term "inhibit" means to decrease the amount, quality, or effect of a particular activity and is used interchangeably with the terms "reduce", "minimize", and "lessen" and refers to, for example, the reduction of osteoclast bone erosion activity caused by the administration of a therapeutically effective amount of the compounds of the present invention to a patient.

As used herein, the term "alkyl" refers to a saturated branched, straight chain or cyclic hydrocarbon group. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are ($C_1$–$C_5$) alkyl, with ($C_1$–$C_3$) being particularly preferred.

As used herein, the term "substituted alkyl" refers to an alkyl group wherein one or more hydrogen atoms are each independently replaced with other substituents.

As used herein, the term "alkenyl" refers to an unsaturated branched, straight chain or cyclic hydrocarbon group having at least one carbon-carbon double bond. The group may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is ($C_1$–$C_6$) alkenyl, with ($C_1$–$C_3$) being particularly preferred.

As used herein, the term "alkynyl" refers to an unsaturated branched, straight chain or cyclic hydrocarbon group having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is ($C_1$–$C_6$) alkynyl, with ($C_1$–$C_3$) being particularly preferred.

As used herein, the term "substituted alkynyl" refers to an alkynyl group wherein one or more hydrogen atoms are each independently replaced with other substituents.

As used herein, the term "alkoxy" refers to an —OR group, where R is alkyl, alenyl or alkynyl, as defined above.

As used herein, the term "aromatic moiety" refers to a moiety having an unsaturated cyclic hydrocarbon group which has a conjugated (4n=2) π electron system. typical aromatic moieties include, but are not limited to, benzene, naphthalene, anthracene, azulene, indacene, and the like. In preferred embodiments, the aromatic moiety contains 5–20 carbons in the ring system, with 5–10 carbon atoms being particularly preferred.

As used herein, the term "substituted aromatic moiety" refers to an aromatic moiety wherein one or more hydrogen atoms are each independently replaced with other substituents.

As used herein, the term "heteroaromatic moiety" refers to an aromatic moiety wherein one or more of the ring carbon atoms is replaced with another atom such as N, O or S. Typical heteroaromatic moieties include, but are not limited to, pyran, pyrazole, pyridine, pyrrolke, pyrazine, pyridazine, pyrimidine, pyrrolizine, quinazoline, quinoline, quinolizine, quinoxaline, selenophene, thiophere, tellurophene, xanthene and the like.

As used herein, the term "substituted heteroaromatic moiety" refers to a heteroaromatic moiety wherein one or more hydrogen atoms are each independently replaced with other substituents.

Applicants have discovered that the peptides described infra are useful to inhibit osteoclastogenesis and/or osteoclast function. By inhibiting osteoclastogenesis and/or osteoclast function, bone erosion can be minimized or even prevented, and bone loss can be reduced. Patients suffering from diseases characterized by bone loss can be treated by administering an amount of compound effective to inhibit osteoclastogenesis and/or osteoclast function. In addition, patients identified as being susceptible to diseases characterized by bone loss can be prophylactically treated by administering an amount of compound effective to inhibit osteoclastogenesis and/or osteoclast function.

Individuals who have a disease characterized by bone loss can be identified by those having ordinary skill in the art by well known diagnostic means and criteria. Individuals who are susceptible to a disease characterized by bone loss can be identified by those having ordinary skill in the art based upon family medical history and/or the presence of genetic markers or genes associated with a disease characterized by bone loss.

According to the invention, TRANCE/RANK inhibitors useful in the invention are compounds described infra such as peptides and peptide analogues designed from a binding loop of a TNF-R superfamily member which function to inhibit osteoclastogenesis and/or osteoclast function. Such compounds may be produced by the methods described infra or by other techniques well known to those skilled in the art.

According to the invention, TRANCE/RANK inhibitors useful in the invention to treat diseases characterized by bone loss may be formulated and administered in the manner taught infra, or by other techniques well known to those skilled in the art.

According to the invention, TRANCE/RANK inhibitors useful in the invention to treat diseases characterized by bone loss may be formulated and administered in the manner taught infra, or by other techniques well known to those skilled in the art. Some preferred dosages range from 1 nM to 500 mM. Some preferred dosages range from 1 mM to 500 mM. Some preferred dosages range from 1 mg to 500 mg. Some preferred dosages range from 1000 mg to 3000 mg. Some preferred dosages range from 1500 mg to 2500 mg. According to the invention, TRANCE/RANK inhibitors are administered one to four times per day.

Pharmaceutical compositions according to the present invention comprise TRANCE/RANK inhibitors formulated in therapeutically effective doses. In some embodiments, the pharmaceutical composition is sterile and pyrogen free.

Other aspects of the present invention include the use of TRANCE/RANK-inhibitors in methods involving other cell types in which TRANCE/RANK-mediated signaling is involved in cell development and/or activity. Such cell types include antigen presenting cells such as dendritic cells and lymphocytes. Anderson et al. (Nature 390:175–179, 1997) refer to the RANK/RANKL in T cells and dendritic cells. Similarly, Kong et al. (Immunol. and Cell Biology 77:188–193, 1999) refer to osteoprotegerin ligand as a common link between osteoclastogenesis, lymph node formation and lymphocyte development. In addition, Wong et al. (J. Leukocyte Biology 65:715–724, 1999) refer to TRANCE as regulating dendritic cell and osteoclast function. TRANCE/RANK inhibitors formulated in effective doses as described supra can be used to modulate dendritic cell maturation and function, T cell proliferation and CD40 receptor systems.

TNF exerts its biological activities by binding to two TNF-R: p55 and p75. A comparison of these receptors with several other cell surface receptors revealed certain shared structural features that led to their classification as a superfamily (Beutler et al., Science 264:667, 1994). The TNF-R superfamily members possess characteristic extracellular Cys-rich domains, yet share only about 25% sequence homology. There are at least ten members in this superfamily, including: TNF-R p55 and p75, TNF-R related protein (rp), CD40, Fas antigen (CD95), low-affinity nerve growth factor receptor (p74), CD27, CD30, 4-1BB and OX40 (Beutler et al., Ann. NY Acad. Sci. pp. 118–133, 1994; Gruss and Dower, Cytokines and Mol. Ther. 1:75–105, 1995).

Loops and turns in many proteins have been shown to play functionally important roles in protein-protein interactions. In a specific embodiment illustrated by way of examples, infra, cyclic peptides were designed from three binding loops of TNF-R p55 which inhibited the binding of TNF to its cellular receptors. In particular, peptides designed from loop 1 of domain 3 exhibited the strongest inhibitory activities. When a peptide designed from this binding loop was used in combination with peptides designed from two other loops, no further increase in inhibitory effects were observed, indicating that loop 1 of domain 3 is a dominate ligand binding site in TNF-R.

Based on this finding, corresponding regions of other TNF-R superfamily members from which inhibitory peptides and peptide analogues can be designed are readily identified by amino acid sequence alignment with the three specific binding sites of TNF-R p55 (FIG. 1). Since the dominate binding site of TNF-R p55 falls within amino acid residues #119 to 136, which sequence starts and ends with Cys, the same region in each TNF-R superfamily member may be used to design peptides and peptide analogues that are within the scope of the present invention. In cases where the regions do not start or end with Cys, the region may extend to then next Cys. For example, the corresponding region in Fas is deleted, and thus this region in starts at residue #97 and ends with #143. In the case of NGF-R, the region ends at the Cys at position at 135. Additionally, residues 74–81 and 97–110 may also be used to design additional peptides and peptide analogues within the scope of the present invention. Such compounds are then cyclized and modified at their termini with hydrophobic moieties as described in greater detail below.

Peptides and Peptide Analogues Designed from Binding Loops of a TNF-R Superfamily Member Generally, a compound used in the present invention is a cyclic peptide or peptide analogue, such as those disclosed in U.S. application Ser. No. 60/146,090, filed Jul. 28, 1999, which is hereby incorporated by reference in its entirety. The peptide or peptide analogue is modified at its termini with hydrophobic moieties. In embodiments wherein the compound is a peptide, the peptide corresponds in primary sequence to a binding loop of a member of the TNF-R superfamily of a portion thereof. In a preferred embodiment, the peptide corresponds in primary sequence to a binding loop of TNF-R p55 or a portion thereof. In certain embodiments, one or more amino acid residues within the peptide are substituted with other amino acid residues. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class, as will be described more thoroughly below. In embodiments wherein the compound is a peptide analogue, the analogue is obtained by replacing at least one amide linkage in the peptide with a substituted amide or an isostere of amide.

In an illustrative embodiment, a compound used in the invention has the following formula:

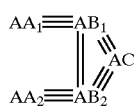

(I)

wherein:

AC is a peptide of 3–18 amino acid residues, preferably 5–8 amino acid residues, which corresponds in primary sequence to a binding loop of a TNF-R and which may optionally contain conservative amino acid substitutions, or an analogue thereof wherein at least one amide linkage is replaced with a substituted amide or an isostere of amide;

$AB_1$ is a moiety having a first functional group capable of forming a covalent linkage with one terminus of AC, a second functional group capable of forming a covalent linkage with $AB_2$ and a third functional group capable of forming a covalent linkage with $AA_1$;

$AB_2$ is a moiety having a first functional group capable of forming a covalent linkage with the second terminus of AC, a second functional goup capable of forming a covalent linkage with $AB_1$ and a third functional group capable of forming a covalent linkage with $AA_2$;

$AA_1$ is a moiety having hydrophobic properties and a functional group capable of forming a covalent linkage with the third functional group of $AB_2$; $AA_2$ is a moiety having hydrophobic properties and a functional group capable of forming a covalent linkage with the third functional group of $AB_2$;

"=" is a covalent linkage; and

"≡" is a covalent linkage.

More specifically, the compounds of the invention are illustrated by three specific embodiments having the following formulae:

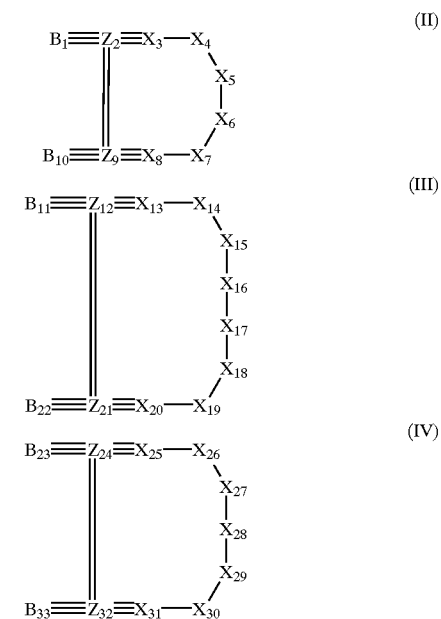

The designation $X_n$ in each case represents an amino acid at the specified position in the compound. Similarly, the designation $Z_n$ represents an amino acid or other moiety which is capable of forming covalent linkages with other $Z_n$, such as disulfide bridges. The amino acid residues denoted by $X_n$ or $Z_n$ may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-alanine | | bAla |
| 2,3-diaminopropionic acid | | Dpr |
| -α-aminoisobutyric acid | | Aib |
| N-Methylglycine (sarcosine) | | MeGly |
| Ornithine | | Orn |

-continued

| Amino Acid | One-Letter Symbol | Common Abbreviation |
|---|---|---|
| Citrulline | | Cit |
| t-buytlalanine | | t-Bua |
| t-butylglycine | | t-Bug |
| N-methylisoleucine | | MeIle |
| phenylglycine | | Phg |
| cyclohexylalanine | | Cha |
| Norleucine | | Nle |
| naphthylalanine | | Nal |
| Pyridylananine | | |
| 3-benzothienylalanine | | |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | 9 |
| Penicillamine | | Pen |
| 1,2,3,4-tetrahydroisoquinoline-3-carboxylic acid | | Tic |
| β-thienylalanine | | Thi |
| Methionine sulfoxide | | MSO |
| Homoarginine | | hArg |
| N-acetyl lysine | | AcLya |
| 2,4-diamino butyric acid | | Dbu |
| p-aminophenylalanine | | Phe(pHN$_2$) |
| N-methylvaline | | MeVal |
| Homocysteine | | hCys |
| Homoserine | | hSer |
| ε-amino hexanoic acid | | Aha |

The compounds used in the invention are partially defined in terms of amino acid residues of designated classes. The amino acids may be generally categorized into three main classes: hydrophilic amino acids, hydrophobic amino acids and Cysteine-like amino acids, depending primarily on the characteristics of the amino acid side chain. These amino classes may be further divided into subclasses. Hydrophilic amino acids include amino acids having acidic, basic or polar side chains and hydrophobic amino acids including amino acids having aromatic or apolar side chains. Apolar amino acids ma be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophyenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (B-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohyxanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (phg); cyclohexylalanine (Cha); norleucine (Nle); 2-naphythylalanine (2-Nal); 4-chlorophenylalanine (Phe(4-Cl)); 2-fluorophenylalanine (Phe(2-F)); 3-flurophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MOS); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F); Pyridyl Ala, Benzothienyl Ala |
| Apolar | M, G, P | T-BuA, T-BuG, MeIle, Nle, |
| Aliphatic | A, V, L, I Aib | MeVal, Cha, bAla, MeGly, |
| Hydrophilic | | |
| Acidic | D, E | Dpr, Orn, hArg, Phe(p-NH$_2$), |
| Basic | H, K, R | DBU, A$_2$BU |
| Polar | Q, N, S, T, Y | Cit, AcLys, MSO, hSer |
| Cysteine-Like | C | Pen, hCys, β-methyl Cys |

The designation $Z_n$ in each case represents an amino acid or other moiety capable of forming covalent linkages with other $Z_n$ so as to allow cyclization of the peptide. Examples of amino acid residues which are capable of forming covalent linkages with one another include cysteine-like amino acids such as Cys, hCys, β-methyl Cys and Pen, which are capable of forming disulfide bridges with one another. Preferred cysteine-like amino acid residues include Cys and Pen.

Amino acids used to cyclize a peptide need not be cysteine-like amino acids. Pairs of amino acids that have side chain functional groups capable of forming covalent linkages with one another can also be used. Such pairs of functional groups are known to those of skill in the art and include, inter alia, —COOH and —OH, —COOH and —NH$_2$, and —COOH and —SH. Thus, pairs of amino acids that can be used to cyclize a peptide include, inter alia, Asp and Lys; Glu and Lys; Asp and Arg; Glu and Arg; Asp and Ser; Glu and Ser; Asp and Thr; Glu and Thr; Asp and Cus; and Glu8 and Cys. Other pairs of amino acids which can be used to cyclize the peptide will be apparent to those skilled in the art.

It will also be recognized that $Z_n$ groups used to cyclize a peptide need not be amino acids. Thus, $Z_n$ may be any molecule having three functional groups—one functional group capable of forming a covalent linkage with a terminus of the peptide, a second functional group capable of forming a covalent linkage with the second functional group of another $Z_n$, and a third functional group capable of forming a covalent linkage with hydrophobic moieties $B_n$. Molecules having a suitable functional groups will be apparent to those skilled in the art. Examples of functional groups capable of forming a covalent linkage with the amino terminus of a peptide include carboxylic acids and esters. Examples of functional groups capable of forming a covalent linkage with the carboxyl terminus of a peptide include —OH, —SH, —NH$_2$ and —NHR where R is (C$_1$–C$_6$) alkyl, (C$_1$–C$_6$) alkenyl and (C$_1$–C$_6$) alkynyl.

A variety of interlinkages useful to cyclize a peptide can be generated by reaction between two $Z_n$. $Z_n$ with functional groups suitable for forming such interlinkages, as well as reaction conditions suitable for forming such interlinkages, will be apparent to those of skill in the art. Preferably, the reaction conditions used to cyclize the peptides are sufficiently mild so as not to degrade or otherwise damage the peptide. Suitable groups for protecting the various functionalities as necessary are well know in the art (see, e.g., Green & Wuts, 1991, $2^{nd}$ ed., John Wiley & Sons NY), as are various reaction schemes for preparing such protected molecules.

The destination $B_n$ in each case represents a hydrophobic moiety. While not intending to be bound by any particular theory, it is believed that when placed in aqueous solution, these hydrophobic moieties interact so as to confer the peptide with structural stability. A significant hydrophobic interaction for conferring structural stability is thought to be stacking of aromatic rings. Thus, in a preferred embodiment, such $B_n$ designates a peptide of 1–6 amino acids, at least one of which is an aromatic amino acid or an aromatic or heteroaromatic moiety. $B_n$ may be illustrated as $X_{32}$–$X_{33}$–$X_{34}$–$X_{35}$–$X_{36}$–$X_{37}$≡ wherein $X_n$ is an amino acid at least one of which is an aromatic amino acid. More preferably, $X_{32}$—$X_{33}$–$X_{34}$—$X_{35}$–$X_{36}$ are absent and $X_{37}$ is an aromatic amino acid. Suitable aromatic amino acids include Tyr, Phe and Trp, with Tyr and Phe being preferred. Suitable aromatic or heteroaromatic moieties include phenyl, naphthyl, purine, pyrimidine, and the like.

In the peptides of formulae (II)–(IV), the symbol "—" between amino acid residues $X_n$ generally designates a backbone interlinkage. Thus, the symbol "—" usually designates an amide linkage (—C(O)—NH). It is to be understood, however, that in all of the peptides described in the specific embodiments herein, one or more amide linkages may optionally be replaced with a linkage other than amide, preferably a substituted amide or an isostere of an amide linkage. Thus, while the various $X_n$ have generally been described in terms of amino acids, one having skill in the art will recognize that in embodiments having non-amide linkages, the term "amino acid" refers to other bifunctional moieties having side-chain groups similar to the side chains of the amino acids. For example, in embodiments having non-amide linkages, the phrase "acidic amino acid" refers to a bifunctional molecule capable of forming the desired backbone interlinkages and which has a side chain group similar to the side chain of an acidic amino acid. Substituted amides generally include groups of the formula —C(O)—NR, where R is (C$_1$–C$_6$) alkyl, (C$_1$–C$_6$) alkenyl, (C$_1$–C$_6$) alkynyl, substituted (C$_1$–C$_6$) alkyl, substituted (C$_1$–C$_6$) alkenyl or substituted (C$_1$–C$_6$) alkynyl. Isosteres of amide generally include, but are not limited to, —CH$_2$NH—, —CH$_2$S—, —CH$_2$CH$_2$, —CH═CH— (cis and trans), —C(O)CH$_2$— and —CH$_2$S)—.

Compounds having such linkages and methods for preparing such compounds are well-known in the art (see, e.g., Spatola, Vega Data 1 (3); 1983, for a general review);

Spatola, "Peptide Backbone Modifications" In: Chemistry and Biochemistry of Amino Acids Peptides and Proteins (Weinstein, ed.), Marcel Dekker, New York, p. 267 (general review) 1983; Morley, Trends Pharm. Sci. 1:463468, 1980; Hudson et al., Int. J. Prot. Res. 14:177–185 (—$CH_2NH$—, —$CH_2CH_2$—)1979; Spatola et al., Life Sci. 38:1243–1249 (—$CH_2$—S), 1986; Hann, J. Chem. Soc. Perkin Trans. I. 1:307–314 (—CH=CH—, cis and trans), 1982; Jennings-White et al., Tetrahedron. Lett. 23:1392–1398 (—$COCH_2$—); European Patent Application EP 45665 (1982) CA:97:39405 (—CH(OH)$CH_2$—); Holladay et al, Tetrahedron Lett. 24:4401–4404, 1983, (—C(OH)$CH_2$—); and Hruby, Life Sci. 31:189–199, 1982 (—$CH_2$—S—).

As will be discussed in more detail below, the interlinkage designated by "≡" between residues $B_n$ and/or $Z_n$ and/or $X_n$ in the compounds of formulae (II)–(IV) may also be a linker. Typically, a linker is a bifunctional molecule that spaces one moiety from another. Such linkers, which may be flexible, semi-rigid or rigid, are well-known in the art and include polypeptides such as poly-Gly and poly-Pro, bifunctional hydrocarbons such as aminocaproic acid, δ-aminovaleric acid and β-alanine, carbohydrates, nucleic acids, and the like.

In one specific illustrative embodiment, the compounds of formula (II) are defined as follows:

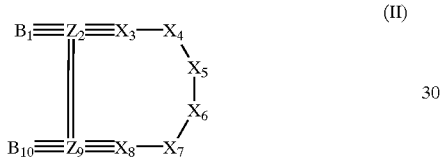

(II)

wherein:
$B_1$ and $B_{10}$ are each independently a peptide of 1–6 amino acids, at least one of which is a hydrophobic amino acid, an aromatic moiety or a heteroaromatic moiety;
$Z_2$ is a moiety that is capable of forming a covalent linkage with $B_1$, $X_3$ and $Z_9$;
$Z_9$ is a moiety that is capable of forming a covalent linkage with $B_{10}$, $X_8$ and $Z_2$;
$X_3$ is absent or a hydrophilic amino acid;
$X_4$ is a hydrophobic amino acid;
$X_5$ is a hydrophilic amino acid;
$X_6$ is a hydrophilic amino acid;
$X_7$ is a hydrophobic or hydrophilic amino acid;
$X_8$ is a hydrophobic or hydrophilic amino acid;
"—" is an amide, substituted amide or an isostere of amide thereof;
"=" is a covalent linkage; and
"≡" is a covalent linkage.

In a preferred embodiment of the invention, the compounds are those of formula (II) wherein:
$B_1$ and $B_{10}$ are each independently a peptide of 1–3 amino acids, at least one of which is an aromatic amino acid;
$Z_2$ and $Z_9$ are each independently a Cys-like amino acid;
$X_3$ is absent or an acidic amino acid;
$X_4$ is an aromatic or apolar amino acid;
$X_5$ is a polar amino acid;
$X_6$ is a polar amino acid;
$X_7$ is an aromatic or polar amino acid;
$X_8$ is an aromatic, apolar or polar amino acid;
"—" is an amide linkage;
"=" is a disulfide linkage; and
"≡" is an amide linkage.

In particularly preferred embodiment, the compounds used in the invention are those of formula (II) wherein:
$B_1$ and $B_{10}$ are each independently Tyr or Phe;
$Z_2$ and $Z_9$ are each Cys;
$X_3$ is absent or Glu;
$X_4$ is Trp or Leu;
$X_5$ is Ser;
$X_6$ is Gln;
$X_7$ is Tyr or Asn;
$X_8$ is Tyr or Leu;
"—" is an amide linkage;
"=" is a disulfide linkage; and
"≡" is an amide linkage.

Particularly preferred peptides used in the invention include the following:

```
YCELSQYLCY      (SEQ ID NO:12)
YC WSQNLCY      (SEQ ID NO:13)
YC WSQNYCY      (SEQ ID NO:14)
YC WSQYLCY      (SEQ ID NO:15)
```

In a second illustrative embodiment, the compounds of formula (III) are defined as follows:

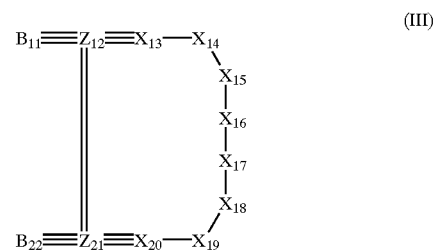

(III)

wherein:
$B_{11}$ and $B_{22}$ are each independently a peptide of 1–6 amino acids, at least one of which is a hydrophobic amino acid, an aromatic moiety or a heteroaromatic moiety;
$Z_{12}$ is a moiety that is capable of forming a covalent linkage with $B_{11}$, $X_{13}$ and $Z_{21}$;
$Z_{21}$ is a moiety that is capable of forming a covalent linkage with $B_{22}$, $X_{20}$ and $Z_{12}$;
$X_{13}$ is absent or hydrophobic amino acid;
$X_{14}$ is absent or a hydrophilic amino acid;
$X_{15}$ is a hydrophilic or hydrophobic amino acid;
$X_{16}$ is hydrophilic amino acid;
$X_{17}$ is absent or a hydrophobic amino acid;
$X_{18}$ is a hydrophilic amino acid;
$X_{19}$ is a hydrophilic amino acid;
$X_{20}$ is a hydrophilic amino acid;
"—" is an amide, a substituted amide or an isostere of amide thereof;

In a preferred embodiment, the compounds are those of formula (III) wherein:
$B_{11}$ and $B_{22}$ are each independently a peptide of 1–3 amino acids, at least one of which is an aromatic amino acid;
$Z_{12}$ and $Z_{21}$ are each independently a Cys-like amino acid;

$X_{13}$ is absent or an aromatic amino acid;
$X_{14}$ is absent or a polar amino acid;
$X_{15}$ is a basic, polar or apolar amino acid;
$X_{16}$ is a polar amino acid;
$X_{17}$ is absent or an apolar amino acid;
$X_{18}$ is an acidic amino acid;
$X_{19}$ is a polar amino acid;
$X_{20}$ is a basic amino acid;
"—" is an amide linkage;
"=" is a disulfide linkage; and
"≡" is an amide linkage.

In particularly preferred embodiment, the compounds are those of formula (III), wherein:
$B_{11}$ and $B_{22}$ are each independently Tyr or Phe;
$Z_{12}$ and $Z_{21}$ are each Cys;
$X_{13}$ is absent or Phe;
$X_{14}$ is absent or Thr;
$X_{15}$ is Ala, Asn or Arg;
$X_{16}$ is Ser;
$X_{17}$ is absent or Val;
$X_{18}$ is Glu;
$X_{19}$ is Asn;
$X_{20}$ is Arg or His;
"—" is an amide linkage;
"=" is a disulfide linkage; and
"≡" is an amide linkage.

Particularly preferred peptides used in the invention include the following:

```
YC FTASENH CY      (SEQ. ID NO:16)
YC FTNSENH CY      (SEQ. ID NO:17)
YC FTRSENH CY      (SEQ. ID NO:18)
FC    ASENH CY     (SEQ. ID NO:19)
YC    ASENH CY     (SEQ. ID NO:20)
FC    NSENH CY     (SEQ. ID NO:21)
FC    NSENR CY     (SEQ. ID NO:22)
FC    NSVENR CY    (SEQ. ID NO:23)
```

In a third illustrative embodiment, the compounds of formula (IV) are defined as follows:

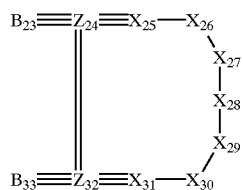

(IV)

wherein:
$B_{23}$ an $B_{33}$ are each independently a peptide of 1–6 amino acids, at least one of which is a hydrophobic amino acid, an aromatic moiety or a heteroaromatic moiety;
$Z_{24}$ is a moiety that is capable of forming a covalent linkage with $B_{23}$, $X_{25}$ and $Z_{32}$;
$Z_{32}$ is a moiety that is capable of forming a covalent linkage with $B_{33}$, $X_{31}$ and $Z_{24}$;
$X_{25}$ is absent or a hydrophilic amino acid;
$X_{26}$ is a hydrophilic amino acid;
$X_{27}$ is a hydrophilic amino acid;
$X_{28}$ is a hydrophobic amino acid;
$X_{29}$ is a hydrophobic amino acid;
$X_{30}$ is absent or a hydrophilic amino acid;
$X_{31}$ is absent or a hydrophobic amino acid;
"—" is an amide, a substituted amide or an isostere of amide;
"=" is a covalent linkage; and
"≡" is a covalent linkage.

In a preferred embodiment, the compounds are those of formula (IV) wherein:
$B_{23}$ an $B_{33}$ are each independently a peptide of 1–3 amino acids, at least one of which is a an aromatic acid;
$Z_{24}$ and $Z_{32}$ are each independently a Cys-like amino acid;
$X_{25}$ is absent or a basic amino acid;
$X_{26}$ is a basic amino acid;
$X_{27}$ is an acidic amino acid;
$X_{28}$ is an apolar amino acid;
$X_{29}$ is an apolar amino acid;
$X_{30}$ is absent or a polar amino acid;
$X_{31}$ is absent or a apolar amino acid;
"—" is an amide linkage;
"=" is a disulfide linkage; and
"≡" is an amide linkage.

In a particularly preferred embodiment, the compounds used in the invention or analogues thereof are those of formula (IV), wherein:
$B_{23}$ an $B_{33}$ are each independently Tyr or Phe;
$Z_{24}$ and $Z_{32}$ are each Cys;
$X_{25}$ is absent or Arg;
$X_{26}$ is Lys;
$X_{27}$ is Glu;
$X_{28}$ is Leu, Pro or Met;
$X_{29}$ is Gly;
$X_{30}$ is absent or Gln;
$X_{31}$ is absent or Val;
"—" is an amide linkage;
"=" is a disulfide linkage; and
"≡" is an amide linkage.

Particularly preferred peptides used in the invention include the following:

```
YC RKELGOV CY      (SEQ. ID NO:24)
YC  KEPGQ  CY      (SEQ. ID NO:25)
YC  RKEMG  CY      (SEQ. ID NO:26)
FC  RKEMG  CY      (SEQ. ID NO:27)
```

In all of the aforementioned embodiments of the invention, it is to be understood at the phrase "amino acid" also refers to bifunctional moieties having amino acid-like side chains, as previously described.

Generally, active peptides or peptide analogues used in the invention are those that exhibit at least about 15% inhibition of TNF-R:TNF interactions as measured in vitro assays such as those described, infra. Preferably, active peptides used in the invention or analogues thereof will exhibit at least about 20% to 50% or even 80% or more inhibition of TNF-R:TNF-α binding interactions.

Preparation Of Peptides And Peptide Analogues

Chemical Synthesis

The peptides used in the invention or analogues thereof, may be prepared using virtually any art-known technique for the preparation of peptides and peptide analogues. For example, the peptides may be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

Formation of disulfide linkages, if desired, is generally conducted in the presence of mild oxidizing agents. Chemical, enzymatic or photolytic oxidation agents may be used. Various methods are known in the art, including those described, for example, by Tam, J. P. et al., Synthesis 955–957, 1979; Stewart et al., Solid Phase Peptide Synthesis. 2d Ed., Pierce Chemical Company Rockford, Ill., 1984; Ahmed et al., J. Biol. Chem. 250:8477–8482, 1975; and Pennington et al. Peptides 1990 164–166, Giralt and Andreu, Eds., ESCOM, 1991; Leiden, The Netherlands. An additional alternative is described by Kamber et al., Helv Chim Acta, 63:899–915, 1980. A method conducted on solid supports is described by Albericio, Int.J. Peptide Protein Res., 26:92–97, 1985. Any of these methods may be used to form disulfide linkages in the peptides of the invention. Preferred methods for effecting disulfide-bridge formation for the peptides described herein are provided in the examples.

Recombinant Synthesis

If the peptide is composed entirely of gene-encoded amino acids, or a portion of it is so composed, the peptide or the relevant portion may also be synthesized using conventional recombinant genetic engineering techniques. The isolated peptides, or segments thereof, are then condensed, and oxidized, as previously described, to yield a cyclic peptide.

For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the linear form of the cyclic peptide. Depending on the expression system used, the expressed peptide is then isolated by procedures well-established in the art. Methods for recombinant protein and peptide production are well known in the art (see, e.g., Maniatis et al., Molecular Cloning A Laboratory Manual, Cold Spring Harbor Laboratory, N.Y., 1989; and Ausubel et al., Current Protocols in Molecular Biology, Greene Publishing Associates and Wiley Interscience, N.Y., 1989).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or Tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of baceriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genomes of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., Nature 310: 511–514, 1984), or the coat protein promoter of TMV (Takamatsu et al., EMBO J., 6:307–311, 1987) may be used; alternatively, plant promoters such as the small subunit of RUBISCO (Coruzzi et al., EMBO J. 3:1671–1680, 1984; Broglie et al., Science 224:838–843, 1984) or heat shock promoters, e.g., soybean hsp17.5-E or hsp17.3-B (Gurley et al., Mol. Cell. Biol. 6:599–565, 1986) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, Methods for Plant Molecular Biology, Academic Press, NY, Section VIII, pp. 421–463, 1988; and Grierson & Corey, Plant Molecular Biology, $2^{nd}$ Ed., Blackie, London, Ch. 7–9, 1988.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successfuil insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al, J. Virol., 46:584, 1983; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g.

Region E1 or E3) will result in a recombinant virus that is viable and capable of expressing peptide in infected hosts. (e.g., See Logan & Shenk, Proc. Natl. Acad. Sci. USA 81:3655–3659, 1984). Alternatively, the vaccinia 7.5 K promoter may be used, (see, e.g., Mackett et al., Proc. Natl. Acad. Sci. USA, 79:7415–7419, 1982; Mackett et al., J. Virol., 49:857–864, 1984; Panicali et al., Proc. Natl. Acad. Sci. 79:4927–4931, 1982).

Other expression systems for producing linear or non-cyclized forms of the cyclic peptides used in the invention will be apparent to those having skill in the art.

Purification of the Peptides and Peptide Analogues

The peptides and peptide analogues used in the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the peptides or peptide analogues may be used. For the production of antibodies, various host animals, including but not limited to rabbits, mice, rats, etc., may be immunized by injection with a linear or cyclic peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, sufrace active substances such as lysolecithin, pluronic polyols, polyanions, peptides, oil emulsions, keyhole limpet hemocyanin, dinitrophenol, and potentially useful human adjuvants such as BCG (bacilli Calmette-Duerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, Nature, 256:495–497, 1975; the human B-cell hybridoma technique, Kosbor et al., Immunology Today, 4:72, 1983; Cote et al., Proc. Natl. Acad. Sci., USA, 80:2026–2030, 1983; and the EBV-hybridoma technique (Cole et al., Monoclonal Antibodies and Cancer Therapy, Alan R. Liss, Inc., pp. 77–96 (1985)). In addition, techniques developed for the production of "chimeric antibodies" (Morrison et al., Proc. Natl. Acad. Sci., USA, 81: 6851–6855, 1984; Neuberger et al., Nature, 312:604–608, 1984; Takada et al., Nature, 314:452–454, 1985) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cyclic peptide-specific single chain antibodies.

Antibody fragments which contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., Science 246: 1275–1281, 1989) to allow rapid and easy identification of monoclonal Fab fragments with the desired specificity for the cyclic peptide of interest.

The antibody or antibody fragment specific for the desired cyclic peptide can be attached, for example, to agarose, and the antibody-agarose complex is used in immunochromatography to purify cyclic peptides of the invention. See, Scopes, *Protein Purification: Principles and Practice*, Spriger-Verlag New York, Inc., NY, 1984; Livingstone, *Methods Enzymology: Immunoaffinity Chromatoprapfhy of Proteins* 34:723–731, 1974.

Formulation and Route of Administration

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiological acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium, carboxymethylcellulose, and/or polyvinylpyrrolidone (PVP); granulating agents; and binding agents. If desired, disintegrating agents may be added, such as the cross-linked polyvinylpyrrolidone, atgar, or alginic acid or a salt thereof such as sodium alginate.

If desired, solid dosage forms may be sugar-coated or enteric-coated using standard techniques.

For oral preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

Effective Dosages

The compounds of the invention will generally be used in an amount effective to achieve the intended purpose. For use to treat or prevent osteoclastogenesis or osteoclast activity, the compounds of the invention, or pharmaceutical compositions thereof, are administered or applied in a therapeutically effective amount. By therapeutically effective amount is meant an amount which is effective to ameliorate, or prevent the symptoms of the disease or disorder, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of TNF-R: TNF-binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulation a dosage range that is not toxic for use in human. The dosage of the compounds described herein lies preferably within a range of circulating concentrations that include the effective dose with little or not toxicity. The dosage may vary within this range depending upon the dosage form employed and the route of administration utilized. The exact formulation, route of administration and dosage can be chosen by the individual physician in view of the patient's condition. (See, e.g., Fingl et al., In: The Pharmacological Basis of Therapeutics, Ch.1, p.1, 1975).

The invention having been described, the following examples are offered by way of illustration and not limitation.

EXAMPLES

Example 1

Recently, therapeutic peptidomimetics that interfere with the TNF/TNF receptor interaction have been developed based on atomic structures deduced from the crystal structures of TNF-α and the TNF/βTNF receptor complex (Takasaki et al. Nature Biotechnology, 15:1266–1270, 1997). The most critical TNF-α recognition site was localized to the first loop of the third domain of TNF receptor (residues 107–114). A peptidomimetic (WP9QY) engineered to mimic this recognition site efficiently antagonized the effects of TNF-binding to the TNF-α receptor in L929 lymphocytes.

WP9QY peptide was tested at concentrations ranging from about 5 µM to about 500 µM for its effect on osteoclast formation using the co-culture system induced by 1,25OH2D3 (1alpha,25-dihydroxyvitamin D3) and PGE2. Osteoclastogenesis was dose- and time-dependently inhibited by the peptide WP9QY ($IC_{50}$=250 µM), but this $IC_{50}$ was 50-fold higher than what was required for the TNF/TNF receptor interaction (5 µM). This difference suggests that the WP9QY peptide inhibits osteoclastogenesis by interfering not with the TNF/TNF receptor interaction but with another related ligand-receptor pair such as TRANCE/RANK. This was confirmed by demonstrating that WP9QY inhibits TRANCE-induced marrow cultures. There was a reciprocal dose-dependence of WP9QY and TRANCE. Thus, WP9QY is capable of interfering not only with the TNF/TNF receptor interaction but also with the RANK Ligand/RANK interaction, thereby decreasing the osteoclastogenic potential of this cytokine.

Example 2

Materials and Methods

Human recombinant TNF-α and $^{125}$I-labeled TNF-α were obtained from Amersham Life Science, Inc. (Arlington Heights, Ill.). TNF-R(I) or p55 extracellular domain-IgG heavy chain chimeric protein was prepared by expression of a cDNA construct (Peppel et al., J. Exp. Med. 174:1483, 1991; Williams et al., Immunol. 84:433, 1995). Anti-TNF-α monoclonal antibody was prepared according to Doring et al. (Molecular Immunol. 31:1059, 1994) and anti-TNF-R(I) monoclonal antibody (htr-9) was obtained from BMA Biomedicals AG (Augst, Switzerland).

Molecular Modeling

Computer modeling was performed using Quanta 4.0 (Molecular Simulation Inc., MA). The model peptides were constructed from their sequences and folded using CHARMM. The side chains of amino acid residues were first positioned to permitted conformation using Ponders rotamer (Ponder et al., J. Mol. Biol. 193:775–791, 1987) database provided in QUANTA. Then, the folded peptides were minimized to convergence with the dielectric constant set to 80.

The crystal structure of the TNF-β/TNF-R(I) complex (Banner et al., Cell 73:431, 1993) was utilized to determine the binding sites of TNF-R for TNF-α. The first (residues 56–73) and second (residues 76–83) loops of domain 2 and the first loop (residues 107–114) of domain 3 of the TNF-R were explored for use in designing peptides. The essential amino acid sequences of TNF-R for binding interactions with TNF-α were identified as structural templates by superimposing TNF-α to TNF-β complexed with its cognate receptor. Then, 5–8 amino acid-long peptides derived from TNF-R as shown in Table 2 were used as templates for the design of exocyclic peptides. Additional peptides were derived from CDR sequences of a light chain of an anti-TNF-α neutralizing antibody, CDRIL of Di62 (Doring et al., Mol. Immunol. 31:1059, 1994). Exocyclic modifications such as peptide cyclization and addition of aromatic amino acids such as Phe and Tyr to the ends of each peptide were performed as described (Zhang et al., Nature Biotech. 14:472, 1996; Zhang et al., Nature Biotech 15:150, 1997).

Peptide Synthesis, Cyclization and Purification

Linear peptides were synthesized by solid-phase methods, deprotected, and released from the resin utilizing standard methodology well known to those skilled in the art. Peptides were precipitated and purified by high performance liquid chromatography (HPLC) utilizing a C18 column and then lyophilized. The purity of such peptides was greater than 95% as measured by HPLC analysis.

The peptides containing internal Cys residues were oxidized by dissolving them at 100 µg/ml in distilled water adjusted or buffered to pH 8.0–8.5, for example, by $(NH_4)_2CO_3$ with stirring and exposure to air at 4° C. for <10 days until 95% formation of intramolecular disulfide bonds had ben confirmed by DTNB (Sigma, St. Louis, Mo.) which determined free sulfhydryls in peptides (Habeeb, Anal. Bioch. 56:60, 1973; Angeletti et al., In Techniques in Protein Chemistry VII, Ed. Marsak, Academic Press, San Diego, Calif., pp. 81–91, 1996). Briefly, peptides (100 µg/ml, 50 µl) and DTNB (10 mM, 50 µl) were added to 0.1 M sodium phosphate buffer (pH 8.0, 1 ml), incubated in the dark for 30 minutes, and the absorbance at 420 nm was determined and compared with the linear unoxidized peptides.

The cyclized peptides were lyophilized, purified by HPLC utilizing a C18 preparative column and a size exclusion column Protein-Pak 60 (Waters, Milford, Mass.). The purity of the peptides was shown to be greater than 95% by HPLC analysis. The concentration of each cyclized peptide was calculated based on UV intensity versus the corresponding linear peptide by HPLC analysis.

Amino acid sequences corresponding to three TNF-α-binding loops of TNF-R were used as templates for the synthesis of a number of peptides. Cys residues were included in the linear peptides to enable their cyclization. Their identity was verified by mass spectrometry. Various exocyclic peptides are listed in Table 2.

TABLE 2

Amino Acid Sequences of TNF-α Binding Sites in TNF-R and Exocyclic Peptides Derived from These Sites.

| TNF-α Binding Sites in the Receptor | Name | Exocyclic Peptides* | S.I.D. # |
|---|---|---|---|
| Binding Site - 5 | | | |
| TNF-α | WP5 | YC FTASENH CY | 16 |
| 53E 82R 85VSY87 125Q 127E | WP5N | YC FTNSENH CY | 17 |
| | WP5R | YC FTRSENH CY | 18 |
| Receptor (loop 1 of domain 2) | WP5J | FC   ASENH CY | 19 |
| 60 FTASENH 66 | WP5JY | YC   ASENH CY | 20 |
| | WP5JN | FC   NSENH CY | 21 |
| | WP5JR | FC   NSENR CY | 22 |
| | WP5VR | FC   NSVENR CY | 23 |
| | WP1** | YC SQSVSND CF | 28 |
| | WP1R** | FC   VSNDR CY | 29 |

TABLE 2-continued

Amino Acid Sequences of TNF-α Binding Sites in TNF-R and Exocyclic Peptides Derived from These Sites.

| TNF-α Binding Sites in the Receptor | Name | Exocyclic Peptides* | S.I.D. # |
|---|---|---|---|
| Binding site - 8 | | | |
| TNF-α | | | |
| 65K 67Q 113P 115Y 143L 145A | | | |
| | WP8L | YC RKELGQV CY | 24 |
| Receptor (loop 2 of domain 2) | WP8JP | YC KEPGQ CY | 25 |
| 76 CRKEMGOV 83 | WP8J | YC RKEMG CY | 26 |
| | WP8JF | FC RKEMG CY | 27 |
| Binding site - 9 | | | |
| TNF-α | | | |
| 72THVL75 77T 97I 137 N | | | |
| | WP9Q | YC WSQNL CY | 13 |
| Receptor (loop 1 of domain 3) | WP9ELY | YCELSQYL CY | 12 |
| 107 WSENL 111 | WP9Y | YC WSQNY CY | 14 |
| | WP9QY | YC WSQYL CY | 15 |

*Peptides were cyclized with cysteine disulfide bridges
**WP1 and WP1R were derived from an anti-TNF-α antibody (Di62, CDR1L) and the template sequence is QSVSNDV.

Example 3

Identification of Osteoclasts Formed in Vitro

TRAP refers to tartrate resistant acid phosphatase which identifies osteoclast-like cells. Osteoprotegerin (OPG) is a naturally occurring secreted protein with homology to members of the TNF receptor family. Administration of OPG in vivo inhibits osteoclastogenesis and associated bone resorption and blocks the pathological increase in osteoclast numbers and activity seen in animal models that mimic osteopenic disorders in humans. OPG can be used as a positive control in the TRAP assay.

Cytochemical staining for TRAP is widely used for identifying osteoclasts in vivo and in vitro. Naphthol AS-MX phosphate 5 mg. Sigma, St. Louis, Mo.) is resolved in 0.5 ml of N,N-dimethylformamide (Wako). Thirty milligrams of fast red violet LB salt (Sigma) and 50 ml of 0.1 M sodium acetate buffer (pH 5.0) containing 50 mM sodium tartratet are added to the mixture (the TRAP-staining solution). Cells are fixed with 3.7% (v/v) formaldehyde in $Ca^{2-}$- and $Mg^{2+}$-free phosphate-buffered saline [PBS(−)] for 10 min. fixed again with ethanol-acetone (50:50, v:v) for 1 min. and incubated with the TRAP-staining solution for 10 min. at room temperature. TRAP-positive osteoclasts appear as red cells. The incubation period longer than 10 min. should be avoided since cells other than osteoclasts become weakly positive with time. After staining, cells are washed with distilled water, and TRAP-positive multinucleated cells having three or more nuclei are counted as osteoclasts under a microscope. (G. C. Nicholson, J. M. Mosely, P. M. Sexton, F. A. O. Mendelssohn, and T. J. Martin, *J. Clin. Invest.* 78, 355, 1986, which is incorporated herein by reference).

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein in incorporated by reference in their entirety.

We claim:

1. A method of inhibiting osteoclastogenesis comprising the step of administering to a patient an amount of a TRANCE/RANK inhibitor effective to inhibit osteoclastogenesis, wherein the inhibitor has the formula:

$$AA_1 = AB_1 \atop AA_2 = AB_2 \rangle AC \quad (I)$$

wherein:
- AC is a peptide of 3–18 amino acid residues which corresponds in primary sequence to a binding loop of a TNF-R superfamily member, and which may optionally contain one or more amino acid substitutions, or an analogue thereof wherein at least one amide linkage is replaced with a substituted amide or an isostere of amide;
- $AB_1$ is a moiety having a first functional group capable of forming a covalent linkage with one terminus of AC, a second functional group capable of forming a covalent linkage with $AB_2$ and a third functional group capable of forming a covalent linkage with $AA_1$;
- $AB_2$ is a moiety having a first functional group capable of forming a covalent linkage with the second terminus of AC, a second functional group capable of forming a covalent linkage with $AB_1$ and a third functional group capable of forming a covalent linkage with $AA_2$;
- $AA_1$ is a moiety having hydrophobic properties and a functional group capable of forming a covalent linkage with the third functional group of $AB_2$;
- $AA_2$ is a moiety having hydrophobic properties and a functional group capable of forming a covalent linkage with the third functional group of $AB_2$;
- "=" is a covalent linkage; and
- "≡" is a covalent linkage.

2. The method of claim 1 in which the amino acid substitutions are conservative.

3. The method of claim 1 wherein the inhibitor has the formula:

$$B_1 = Z_2 = X_3 - X_4 \atop B_{10} = Z_9 = X_8 - X_7 \rangle X_5 \atop X_6 \quad (II)$$

wherein:
- $B_1$ and $B_{10}$ are each independently a peptide of 1–6 amino acids at least one of which is a hydrophobic amino acid, an aromatic moiety or a heteroaromatic moiety:
- $Z_2$ is a moiety forming a covalent linkage with $B_1$, $X_3$ and $Z_9$;
- $Z_9$ is a moiety forming a covalent linkage with $B_{10}$, $X_8$ and $Z_2$;
- $X_3$ is absent or a hydrophilic amino acid;
- $X_4$ is a hydrophobic amino acid;
- $X_5$ is a hydrophobic amino acid;
- $X_6$ is a hydrophobic amino acid;
- $X_7$ is a hydrophobic or hydrophilic amino acid;
- $X_8$ is a hydrophobic or hydrophilic amino acid;
- "—" is an amide, substituted amide or an isostere of amide thereof;
- "=" is a covalent linkage; and
- "≡" is a covalent linkage.

4. The method of claim 3, wherein:
- $B_1$ and $B_{10}$ are each independently a peptide of 1–2 amino acids, at least one of which is an aromatic amino acid;
- $Z_2$ and $Z_9$ are each independently a Cys-like amino acid;
- $X_3$ is absent or an acidic amino acid;
- $X_4$ is an aromatic or apolar amino acid;
- $X_5$ is a polar amino acid;
- $X_6$ is a polar amino acid;
- $X_7$ is an aromatic or polar amino acid;
- $X_8$ is an aromatic, apolar or polar amino acid;
- "—" is an amide linkage;
- "=" is a disulfide linkage; and
- "≡" is an amide linkage.

5. The method of claim 4, wherein:
- $B_1$ and $B_{10}$ are each independently Tyr or Phe;
- $Z_2$ and $Z_9$ are each Cys;
- $X_3$ is absent or Glu;
- $X_4$ is Trp or Leu;
- $X_5$ is Ser;
- $X_6$ is Gln;
- $X_7$ is Tyr or Asn;
- $X_8$ is Tyr or Leu;
- "—" is an amide linkage;
- "=" is a disulfide linkage; and
- "≡" is an amide linkage.

6. The method of claim 5, wherein said inhibitor is selected from the group consisting of WP9Q—SEQ ID NO:13, WP9ELY—SEQ ID NO:12, WP9Y—SEQ ID NO:14, and WP9QY—SEQ ID NO:15.

7. The method of claim 1, wherein the inhibitor has the formula:

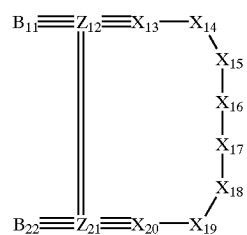

(III)

wherein:
- $B_{11}$ and $B_{22}$ are each independently a peptide of 1–6 amino acids, at least one of which is a hydrophobic amino acid, an aromatic moiety or a heteroaromatic moiety;
- $Z_{12}$ is a moiety forming a covalent linkage with $B_{11}$, $X_{13}$ and $Z_{21}$;
- $Z_{21}$ is a moiety forming a covalent linkage with $B_{22}$, $X_{20}$ and $Z_{12}$;
- $X_{13}$ is absent or hydrophobic amino acid;
- $X_{14}$ is absent or hydrophilic amino acid;
- $X_{15}$ is a hydrophilic or hydrophobic amino acid;
- $X_{16}$ is a hydrophilic amino acid;
- $X_{17}$ is absent or a hydrophobic amino acid;
- $X_{18}$ is a hydrophilic amino acid;
- $X_{19}$ is a hydrophilic amino acid;
- $X_{20}$ is a hydrophilic amino acid;
- "—" is an amide, a substituted amide or an isostere of amide thereof;
- "=" is a covalent linkage; and
- "≡" is a covalent linkage.

8. The method of claim 7, wherein:
- $B_{11}$ and $B_{22}$ are each independently a peptide of 1–3 amino acids, at least one of which is an aromatic amino acid;
- $Z_{12}$ and $Z_{21}$ are each independently a Cys-like amino acid;
- $X_{13}$ is absent or an aromatic amino acid;
- $X_{14}$ is absent or a polar amino acid;
- $X_{15}$ is a basic, polar or apolar amino acid;
- $X_{16}$ is a polar amino acid;
- $X_{17}$ is absent or an apolar amino acid;
- $X_{18}$ is an acidic amino acid;
- $X_{19}$ is a polar amino acid;
- $X_{20}$ is a basic amino acid;
- "—" is an amide linkage;
- "=" is a disulfide linkage; and
- "≡" is an amide linkage.

9. The method of claim 8, wherein:
- $B_{11}$ and $B_{22}$ are each independently Tyr or Phe;
- $Z_{12}$ and $Z_{21}$ are each Cys;
- $X_{13}$ is absent or Phe;
- $X_{14}$ is absent or Thr;
- $X_{15}$ is Ala, Asn or Arg;
- $X_{16}$ is Ser;
- $X_{17}$ is absent or Val;
- $X_{18}$ is Glu;
- $X_{19}$ is Asn;
- $X_{20}$ is Arg or His;
- "—" is an amide linkage;
- "=" is a disulfide linkage; and
- "≡" is an amide linkage.

10. The method of claim 9, wherein said inhibitor is selected from the group consisting of WP5—SEQ ID NO:16, WP5N—SEQ ID NO:17, WP5R—SEQ ID NO:18, WP5J—SEQ ID NO:19, WP5JY—SEQ ID NO:20, WP5JN—SEQ ID NO:21, WP5JR—SEQ ID NO:22, and WP5VR—SEQ ID NO:23.

11. The method of claim 1, wherein the inhibitor has the formula:

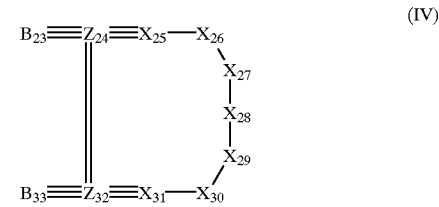

(IV)

- $B_{23}$ and $B_{33}$ are each independently a peptide of 1–6 amino acids, at least one of which is a hydrophobic amino acid, an aromatic moiety or a heteroaromatic moiety;
- $Z_{24}$ is a moiety forming a covalent linkage with $B_{23}$, $X_{25}$ and $Z_{32}$;
- $Z_{32}$ is a moiety forming a covalent linkage with $B_{33}$, $X_{31}$ and $Z_{24}$;
- $X_{25}$ is absent or a hydrophilic amino acid;
- $X_{26}$ is a hydrophilic amino acid;
- $X_{27}$ is a hydrophilic amino acid;
- $X_{28}$ is a hydrophilic amino acid;
- $X_{29}$ is a hydrophilic amino acid;
- $X_{30}$ is absent or a hydrophilic amino acid;
- $X_{31}$ is absent or a hydrophilic amino acid;
- "—" is an amide, a substituted amide or an isostere of amide;
- "=" is a covalent linkage; and
- "≡" is a covalent linkage.

12. The method of claim 11, wherein:
- $B_{23}$ and $B_{33}$ are each independently a peptide of 1–3 amino acids, at least one of which is an aromatic amino acid;
- $Z_{24}$ and $Z_{32}$ are each independently a Cys-like amino acid;
- $X_{25}$ is absent or a basic amino acid;
- $X_{26}$ is a basic amino acid;
- $X_{27}$ is an acidic amino acid;
- $X_{28}$ is an apolar amino acid,
- $X_{29}$ is an apolar amino acid;
- $X_{30}$ is absent or a polar amino acid;
- $X_{31}$ is absent or an apolar amino acid;
- "—" is an amide linkage'
- "=" is a disulfide linkage; and
- "≡" is an amide linkage.

13. The method of claim 12, wherein:
- $B_{23}$ and $B_{33}$ are each independently Tyr or Phe;
- $Z_{24}$ and $Z_{32}$ are each Cys;
- $X_{25}$ is absent or Arg;

$X_{26}$ is Lys;
$X_{27}$ is Glu;
$X_{28}$ is Leu, Pro or Met;
$X_{29}$ is Gly;
$X_{30}$ is absent or Gln;
$X_{31}$ is absent or Val;
"—" is an amide linkage;
"=" is a disulfide linkage; and
"≡" is an amide linkage.

14. The method of claim 13, wherein said inhibitor is selected from the group consisting of WP8L—SEQ ID NO:24, WP8JP—SEQ ID NO:25, WP8J—SEQ ID NO:26, and WP8JF—SEQ ID NO:27.

15. A method of treating patients who have diseases characterized by bone loss comprising the step of administering to said patient an amount of a TRANCE/RANK inhibitor effective to inhibit such bone loss, wherein said inhibitor is a compound having the formula:

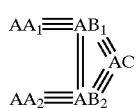

(I)

wherein:
AC is a peptide of 3–18 amino acid residues which corresponds in primary sequence to a binding loop of TNF-R(I), and which may optionally contain one or more amino acid substitutions, or an analogue thereof wherein at least one amide linkage is replaced with a substituted amide or an isostere of amide;
$AB_1$ is a moiety having a first functional group forming a covalent linkage with one terminus of AC, a second functional group forming a covalent linkage with $AB_2$ and a third functional group forming a covalent linkage with $AA_1$;
$AB_2$ is a moiety having a first functional group forming a covalent linkage with the second terminus of AC, a second functional group forming a covalent linkage with $AB_1$ and a third functional group forming a covalent linkage with $AA_2$;
$AA_1$ is a moiety having hydrophobic properties and a functional group forming a covalent linkage with the third functional group of $AB_1$;
$AA_2$ is a moiety having hydrophobic properties and a functional group forming a covalent linkage with the third functional group of $AB_2$;
"=" is a covalent linkage; and
"≡" is a covalent linkage.

16. The method of claim 15 wherein the compound has the formula:

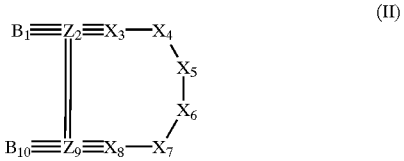

(II)

wherein;
$B_1$ and $B_{10}$ are each independently a peptide of 1–6 amino acids, at least one of which is a hydrophobic amino acid, an aromatic moiety or a heteroaromatic moiety;
$Z_2$ is a moiety that is forming a covalent linkage with $B_1$, $X_3$ and $Z_9$;
$Z_9$ is a moiety that is forming a covalent linkage with $B_{10}$, $X_8$ and $Z_2$;
$X_3$ is absent or a hydrophilic amino acid;
$X_4$ is a hydrophobic amino acid;
$X_5$ is a hydrophilic amino acid;
$X_6$ is a hydrophilic amino acid;
$X_7$ is a hydrophobic or hydrophilic amino acid;
$X_8$ is a hydrophobic or hydrophilic amino acid:
"—" is an amide, substituted amide or an isostere of amide thereof;
"=" is a covalent linkage; and
"≡" is a covalent linkage.

17. The method of claim 16 wherein:
$B_1$ and $B_{10}$ are each independently a peptide of 1–3 amino acids, at least one of which is an aromatic amino acid;
$Z_2$ and $Z_9$ are each independently a Cys-like amino acid;
$X_3$ is absent or an acidic amino acid;
$X_4$ is an aromatic or apolar amino acid;
$X_5$ is a polar amino acid;
$X_6$ is a polar amino acid;
$X_7$ is an aromatic or polar amino acid;
$X_8$ is an aromatic, apolar or polar amino acid;
"—" is an amide linkage;
"=" is a disulfide linkage; and
"≡" is an amide linkage.

18. The method of claim 17 wherein:
$B_1$ and $B_{10}$ are each independently Tyr or Phe;
$Z_2$ and $Z_9$ are each Cys;
$X_3$ is absent or Glu;
$X_4$ is Trp or Leu;
$X_5$ is Ser;
$X_6$ is Gln;
$X_7$ is Tyr or Asn;
$X_8$ is Tyr or Leu;
"—" is an amide linkage;
"=" is a disulfide linkage; and
"≡" is an amide linkage.

19. The method of claim 15 wherein the compound is selected from the group consisting of WP9Q—SEQ ID NO: 13, WP9ELY—SEQ ID NO: 12, WP9Y—SEQ ID NO: 14, and WP9QY—SEQ ID NO: 15.

20. The method of claim 15 wherein the compound has the formula:

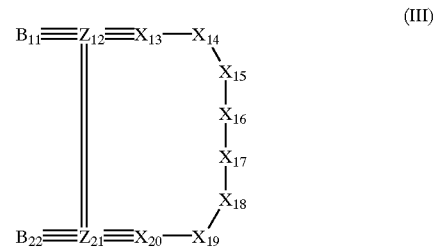

(III)

wherein:
$B_{11}$ and $B_{22}$ are each independently a peptide of 1–6 amino acids, at least one of which is a hydrophobic amino acid, an aromatic moiety or a heteroaromatic moiety;

$Z_{12}$ is a moiety forming a covalent linkage with $B_{11}$, $X_{13}$ and $Z_{21}$;

$Z_{21}$ is a moiety forming a covalent linkage with $B_{22}$, $X_{20}$ and $Z_{12}$;

$X_{13}$ is absent or hydrophobic amino acid;

$X_{14}$ is absent or a hydrophilic amino acid;

$X_{15}$ is a hydrophilic or hydrophobic amino acid;

$X_{16}$ is a hydrophilic amino acid;

$X_{17}$ is absent or a hydrophobic amino acid;

$X_{18}$ is a hydrophilic amino acid;

$X_{19}$ is a hydrophilic amino acid;

$X_{20}$ is a hydrophilic amino acid;

"—" is an amide, a substituted amide or an isostere of amide thereof;

"=" is a covalent linkage; and

"≡" is a covalent linkage.

21. The method of claim 20 wherein:

$B_{11}$ and $B_{12}$ are each independently a peptide of 1–3 amino acids, at least one of which is an aromatic amino acid;

$Z_{12}$ and $Z_{21}$ are each independently a Cys-like amino acid;

$X_{13}$ is absent or an aromatic amino acid;

$X_{14}$ is absent or a polar amino acid;

$X_{15}$ is a basic, polar or apolar amino acid;

$X_{16}$ is a polar amino acid;

$X_{17}$ is absent or an apolar amino acid;

$X_{18}$ is an acidic amino acid;

$X_{19}$ is a polar amino acid;

$X_{20}$ is a basic amino acid;

"—" is an amide linkage;

"=" is a disulfide linkage; and

"≡" is an amide linkage.

22. The method of claim 21 wherein:

$B_{11}$ and $B_{22}$ are each independently Tyr or Phe;

$Z_{12}$ and $Z_{21}$ are each Cys;

$X_{13}$ is absent or Phe;

$X_{14}$ is absent or Thr;

$X_{15}$ is Ala, Asn or Arg;

$X_{16}$ is Ser;

$X_{17}$ is absent or Val;

$X_{18}$ is Glu;

$X_{19}$ is Asn;

$X_{20}$ is Arg or His;

"—" is an amide linkage;

"=" is a disulfide linkage; and

"≡" is an amide linkage.

23. The method of claim 22 wherein the inhibitor is selected from the group consisting of WP5—SEQ ID NO: 16, WP5N—SEQ ID NO: 17, WP5R—SEQ ID NO: 18, WP5J—SEQ ID NO: 19, WP5JY—SEQ ID NO: 20, WP5JN—SEQ ID NO: 21, WP5JR—SEQ ID NO: 22, and WP5VR—SEQ ID NO: 23.

24. The method of claim 15 wherein the compound has the formula:

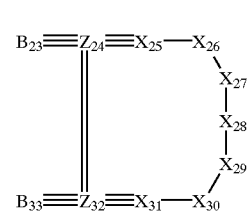

(IV)

wherein:

$B_{23}$ and $B_{33}$ are each independently a peptide of 1–6 amino acids, at least one of which is a hydrophobic amino acid, an aromatic moiety or a heteroaromatic moiety;

$Z_{24}$ is a moiety of forming a covalent linkage with $B_{23}$, $X_{26}$ and $Z_{32}$;

$Z_{32}$ is a moiety of forming a covalent linkage with $B_{33}$, $X_{31}$ and $Z_{24}$;

$X_{25}$ is absent or a hydrophilic amino acid;

$X_{26}$ is a hydrophilic amino acid;

$X_{27}$ is a hydrophilic amino acid;

$X_{28}$ is a hydrophobic amino acid;

$X_{29}$ is a hydrophobic amino acid;

$X_{30}$ is absent or a hydrophobic amino acid;

$X_{31}$ is absent or a hydrophobic amino acid;

"—" is an amide, a substituted amide or an isostere of amide;

"=" is a covalent linkage; and

"≡" is a covalent linkage.

25. The method of claim 24 wherein:

$B_{23}$ and $B_{33}$ are each independently a peptide of 1–3 amino acids, at least one of which is an aromatic amino acid;

$Z_{24}$ and $Z_{32}$ are each independently a Cys-like amino acid;

$X_{25}$ is absent or a basic amino acid;

$X_{26}$ is a basic amino acid;

$X_{27}$ is an acidic amino acid;

$X_{28}$ is an apolar amino acid;

$X_{29}$ is an apolar amino acid;

$X_{30}$ is absent or a polar amino acid;

$X_{31}$ is absent or as apolar amino acid;

"—" is an amide linkage;

"=" is a disulfide linkage; and

"≡" is an amide linkage.

26. The method of claim 25 wherein:

$B_{23}$ and $B_{33}$ are each independently Tyr or Phe;

$Z_{24}$ and $Z_{32}$ are each Cys;

$X_{25}$ is absent or Arg;

$X_{26}$ is Lys;

$X_{27}$ is Glu;

$X_{28}$ is Leu, Pro or Met;

$X_{29}$ is Gly;

$X_{30}$ is absent or Gln;

$X_{31}$ is absent or Val;

"—" is an amide linkage;

"=" is a disulfide linkage; and

"≡" is an amide linkage.

27. The method of claim 26 wherein the inhibitor is selected from the group consisting of WP8L—SEQ ID NO:24.

28. A method of inhibiting bone resorption comprising the step of administering to a patient a TRANCE/RANK amount of an inhibitor effective to inhibit bone resorption, wherein said inhibitor has the formula:

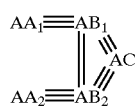

(I)

wherein:
- AC is a peptide of 3–18 amino acid residues which corresponds in primary sequence to a binding loop of TNF-R(I), and which may optionally contain one or more amino acid substitutions, or an analogue thereof wherein at least one amide linkage is replaced with a substituted amide or an isostere of amide;
- $AB_1$ is a moiety having a first functional group forming a covalent linkage with one terminus of AC, a second functional group forming a covalent linkage with $AB_2$ and a third functional group forming a covalent linkage with $AA_1$;
- $AB_2$ is a moiety having a first functional group forming a covalent linkage with the second terminus of AC, a second functional group forming a covalent linkage with $AB_1$ and a third functional group forming a covalent linkage with $AA_2$;
- $AA_1$ is a moiety having hydrophobic properties and a functional group forming a covalent linkage with the third functional group of $AB_2$;
- $AA_2$ is a moiety having hydrophobic properties and a functional group forming a covalent linkage with the third functional group of $AB_2$;
- "=" is a covalent linkage; and
- "≡" is a covalent linkage.

29. The method of claim 28 in which the amino acid substitutions are conservative.

30. The method of claim 28 wherein the inhibitor has the formula:

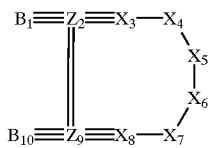

(II)

wherein:
- $B_1$ and $B_{10}$ are each independently a peptide of 1–6 amino acids at least one of which is a hydrophobic amino acid, an aromatic moiety or a heteroaromatic moiety;
- $Z_2$ is a moiety forming a covalent linkage with $B_1$, $X_3$ and $Z_9$;
- $Z_9$ is a moiety forming a covalent linkage with $B_{10}$, $X_8$ and $Z_2$;
- $X_3$ is absent or a hydrophilic amino acid;
- $X_4$ is a hydrophobic amino acid;
- $X_5$ is a hydrophobic amino acid;
- $X_6$ is a hydrophobic amino acid;
- $X_7$ is a hydrophobic or hydrophilic amino acid;
- $X_8$ is a hydrophobic or hydrophilic amino acid;
- "—" is an amide, substituted amide or an isostere of amide thereof;
- "=" is a covalent linkage; and
- "≡" is a covalent linkage.

31. The method of claim 30, wherein:
- $B_1$ and $B_{10}$ are each independently a peptide of 1–2 amino acids, at least one of which is an aromatic amino acid;
- $Z_2$ and $Z_9$ are each independently a Cys-like amino acid;
- $X_3$ is absent or an acidic amino acid;
- $X_4$ is an aromatic or apolar amino acid;
- $X_5$ is a polar amino acid;
- $X_6$ is a polar amino acid;
- $X_7$ is an aromatic or polar amino acid;
- $X_8$ is an aromatic, apolar or polar amino acid;
- "—" is an amide linkage;
- "=" is a disulfide linkage; and
- "≡" is an amide linkage.

32. The method of claim 31, wherein:
- $B_1$ and $B_{10}$ are each independently Tyr or Phe;
- $Z_2$ and $Z_9$ are each Cys;
- $X_3$ is absent or Glu;
- $X_4$ is Trp or Leu;
- $X_5$ is Ser;
- $X_6$ is Gln;
- $X_7$ is Tyr or Asn;
- $X_8$ is Tyr or Leu;
- "—" is an amide linkage;
- "=" is a disulfide linkage; and
- "≡" is an amide linkage.

33. The method of claim 32, wherein said inhibitor is selected from the group consisting of WP9Q—SEQ ID NO:13, WP9ELY—SEQ ID NO:12, WP9Y—SEQ ID NO:14, and WP9QY—SEQ ID NO:15.

34. The method of claim 28, wherein the inhibitor has the formula:

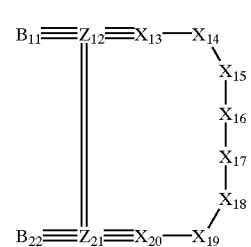

(III)

wherein:
- $B_{11}$ and $B_{22}$ are each independently a peptide of 1–6 amino acids, at least one of which is a hydrophobic amino acid, an aromatic moiety or a heteroaromatic moiety;
- $Z_{12}$ is a moiety forming a covalent linkage with $B_{11}$, $X_{13}$ and $Z_{21}$;
- $Z_{21}$ is a moiety forming a covalent linkage with $B_{22}$, $X_{20}$ and $Z_{12}$;
- $X_{13}$ is absent or hydrophobic amino acid;
- $X_{14}$ is absent or hydrophilic amino acid;
- $X_{15}$ is a hydrophilic or hydrophobic amino acid;
- $X_{16}$ is a hydrophilic amino acid;
- $X_{17}$ is absent or a hydrophobic amino acid;
- $X_{18}$ is a hydrophilic amino acid;
- $X_{19}$ is a hydrophilic amino acid;

$X_{20}$ is a hydrophilic amino acid;

"—" is an amide, a substituted amide or an isostere of amide thereof;

"=" is a covalent linkage; and

"≡" is a covalent linkage.

35. The method of claim 34, wherein:

$B_{11}$ and $B_{22}$ are each independently a peptide of 1–3 amino acids, at least one of which is an aromatic amino acid;

$Z_{12}$ and $Z_{21}$ are each independently a Cys-like amino acid;

$X_{13}$ is absent or an aromatic amino acid;

$X_{14}$ is absent or a polar amino acid;

$X_{15}$ is a basic, polar or apolar amino acid;

$X_{16}$ is a polar amino acid;

$X_{17}$ is absent or an apolar amino acid;

$X_{18}$ is an acidic amino acid;

$X_{19}$ is a polar amino acid;

$X_{20}$ is a basic amino acid;

"—" is an amide linkage;

"=" is a disulfide linkage; and

"≡" is an amide linkage.

36. The method of claim 35, wherein:

$B_{11}$ and $B_{22}$ are each independently Tyr or Phe;

$Z_{12}$ and $Z_{21}$ are each Cys;

$X_{13}$ is absent or Phe;

$X_{14}$ is absent or Thr;

$X_{15}$ is Ala, Asn or Arg;

$X_{16}$ is Ser;

$X_{17}$ is absent or Val;

$X_{18}$ is Glu;

$X_{19}$ is Asn;

$X_{20}$ is Arg or His;

"—" is an amide linkage;

"=" is a disulfide linkage; and

"≡" is an amide linkage.

37. The method of claim 36, wherein said inhibitor is selected from the group consisting of WP5—SEQ ID NO:16, WP5N—SEQ ID NO:17, WP5R—SEQ ID NO:18, WP5J—SEQ ID NO:19, WP5JY—SEQ ID NO:20, WP5JN—SEQ ID NO:21, WP5JR—SEQ ID NO:22, and WP5VR—SEQ ID NO:23.

38. The method of claim 28, wherein the inhibitor has the formula:

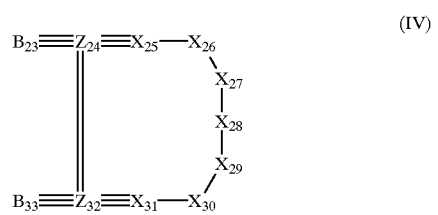

(IV)

wherein:

$B_{23}$ and $B_{33}$ are each independently a peptide of 1–6 amino acids, at least one of which is a hydrophobic amino acid, an aromatic moiety or a heteroaromatic moiety;

$Z_{24}$ is a moiety of forming a covalent linkage with $B_{23}$, $X_{25}$ and $Z_{32}$;

$Z_{32}$ is a moiety of forming a covalent linkage with $B_{33}$, $X_{31}$, and $Z_{24}$;

$X_{25}$ is absent or a hydrophilic amino acid;

$X_{26}$ is a hydrophilic amino acid;

$X_{27}$ is a hydrophilic amino acid;

$X_{28}$ is a hydrophobic amino acid;

$X_{29}$ is a hydrophobic amino acid;

$X_{30}$ is absent or a hydrophobic amino acid;

$X_{31}$ is absent or a hydrophobic amino acid;

"—" is an amide, a substituted amide or an isostere of amide;

"=" is a covalent linkage; and

"≡" is a covalent linkage.

39. The method of claim 38, wherein:

$B_{23}$ and $B_{33}$ are each independently a peptide of 1–3 amino acids, at least one of which is an aromatic amino acid;

$Z_{24}$ and $Z_{32}$ are each independently a Cys-like amino acid;

$X_{25}$ is absent or a basic amino acid;

$X_{26}$ is a basic amino acid;

$X_{27}$ is an acidic amino acid;

$X_{28}$ is an apolar amino acid;

$X_{29}$ is an apolar amino acid;

$X_{30}$ is absent or a polar amino acid;

$X_{31}$ is absent or an apolar amino acid;

"—" is an amide linkage'

"=" is a disulfide linkage; and

"≡" is an amide linkage.

40. The method of claim 39, wherein:

$B_{23}$ and $B_{33}$ are each independently Tyr or Phe;

$Z_{24}$ and $Z_{32}$ are each Cys;

$X_{25}$ is absent or Arg;

$X_{26}$ is Lys;

$X_{27}$ is Glu;

$X_{28}$ is leu, Pro or Met;

$X_{29}$ is Gly;

$X_{30}$ is absent-or Gln;

$X_{31}$ is absent or Val;

"—" is an amide linkage;

"=" is a disulfide linkage; and

"≡" is an amide linkage.

41. The method of claim 40, wherein said inhibitor is selected from the group consisting of WP8L—SEQ ID NO:24, WP8JP—SEQ ID NO:25, WP8J—SEQ ID NO:26, and WP8JF—SEQ ID NO:27.

* * * * *

SEQUENCE LISTING

```
<160> NUMBER OF SEQ ID NOS:  29

<210> SEQ ID NO 1
<211> LENGTH: 74
<212> TYPE: PRT
<213> ORGANISM: Homo sapiens

<400> SEQUENCE: 1

Asp Cys Arg Glu Cys Glu Ser Gly Ser Phe Thr Ala Ser Glu Asn His
  1               5                  10                  15

Leu Arg His Cys Leu Ser Cys Ser Lys Cys Arg Lys Glu Met Gly Gln
             20                  25                  30

Val Glu Ile Ser Ser Cys Thr Val Asp Arg Asp Thr Val Cys Gly Cys
        35                  40                  45
```

Arg Lys Asn Gln Tyr Arg His Tyr Trp Ser Glu Asn Leu Phe Gln Cys
        50                  55                  60

Phe Asn Cys Ser Leu Cys Leu Asn Gly Thr
 65                  70

<210> SEQ ID NO 2
<211> LENGTH: 77
<212> TYPE: PRT
<213> ORGANISM: Homo sapiens

<400> SEQUENCE: 2

Val Cys Asp Ser Cys Glu Asp Ser Thr Tyr Thr Gln Leu Trp Asn Trp
 1               5                  10                  15

Val Pro Glu Cys Leu Ser Cys Gly Ser Arg Cys Ser Ser Asp Gln Val
                20                  25                  30

Glu Thr Gln Ala Cys Thr Arg Glu Gln Asn Arg Ile Cys Thr Cys Arg
            35                  40                  45

Pro Gly Trp Tyr Cys Ala Leu Ser Lys Gln Glu Gly Cys Arg Leu Cys
 50                  55                  60

Ala Pro Leu Arg Lys Cys Arg Pro Gly Phe Gly Val Ala
 65                  70                  75

<210> SEQ ID NO 3
<211> LENGTH: 77
<212> TYPE: PRT
<213> ORGANISM: Homo sapiens

<400> SEQUENCE: 3

Val Cys Ala Thr Cys Ala Glu Asn Ser Tyr Asn Glu His Trp Asn Tyr
 1               5                  10                  15

Leu Thr Ile Cys Gln Leu Cys Arg Pro Cys Asp Pro Val Met Gly Leu
                20                  25                  30

Glu Glu Ile Ala Pro Cys Thr Ser Lys Arg Lys Thr Gln Cys Arg Cys
            35                  40                  45

Gln Pro Gly Met Phe Cys Ala Ala Trp Ala Leu Glu Cys Thr His Cys
 50                  55                  60

Glu Leu Leu Ser Asp Cys Pro Pro Gly Thr Glu Ala Glu
 65                  70                  75

<210> SEQ ID NO 4
<211> LENGTH: 76
<212> TYPE: PRT
<213> ORGANISM: Homo sapiens

<400> SEQUENCE: 4

Cys Glu Pro Cys Leu Asp Ser Val Thr Phe Ser Asp Val Val Ser Ala
 1               5                  10                  15

Thr Glu Pro Cys Lys Pro Cys Thr Glu Cys Val Gly Leu Gln Ser Met
                20                  25                  30

Ser Ala Pro Cys Val Glu Ala Asp Asp Ala Val Cys Arg Cys Ala Tyr
            35                  40                  45

Gly Tyr Tyr Gln Asp Glu Thr Thr Gly Arg Cys Glu Ala Cys Arg Val
 50                  55                  60

Cys Glu Ala Gly Ser Gly Leu Val Phe Ser Cys Gln
 65                  70                  75

<210> SEQ ID NO 5
<211> LENGTH: 53

```
<212> TYPE: PRT
<213> ORGANISM: Homo sapiens

<400> SEQUENCE: 5

Gln Cys Asp Pro Cys Ile Pro Gly Val Ser Phe Ser Pro Asp His His
 1               5                  10                  15

Thr Arg Pro His Cys Glu Ser Cys Arg His Cys Asn Ser Gly Leu Leu
             20                  25                  30

Val Arg Asn Cys Thr Ile Thr Ala Asn Ala Glu Cys Ala Cys Arg Asn
         35                  40                  45

Gly Trp Gln Cys Arg
     50

<210> SEQ ID NO 6
<211> LENGTH: 74
<212> TYPE: PRT
<213> ORGANISM: Homo sapiens

<400> SEQUENCE: 6

Cys Arg Lys Gln Cys Glu Pro Asp Tyr Tyr Leu Asp Glu Ala Asp Arg
 1               5                  10                  15

Cys Thr Ala Cys Val Thr Cys Ser Arg Asp Asp Leu Val Glu Lys Thr
             20                  25                  30

Pro Cys Ala Trp Asn Ser Ser Arg Val Cys Glu Cys Arg Pro Gly Met
         35                  40                  45

Phe Cys Ser Thr Ser Ala Val Asn Ser Cys Ala Arg Cys Phe Phe His
     50                  55                  60

Ser Val Cys Pro Ala Gly Met Ile Val Lys
 65                  70

<210> SEQ ID NO 7
<211> LENGTH: 74
<212> TYPE: PRT
<213> ORGANISM: Homo sapiens

<400> SEQUENCE: 7

Cys Arg Lys Gln Cys Glu Pro Asp Tyr Tyr Leu Asp Glu Ala Gly Arg
 1               5                  10                  15

Cys Thr Ala Cys Val Ser Cys Ser Arg Asp Asp Leu Val Glu Lys Thr
             20                  25                  30

Pro Cys Ala Trp Asn Ser Ser Arg Thr Cys Glu Cys Arg Pro Gly Met
         35                  40                  45

Ile Cys Ala Thr Ser Ala Thr Asn Ser Cys Ala Arg Cys Val Pro Tyr
     50                  55                  60

Pro Ile Cys Ala Ala Glu Thr Val Thr Lys
 65                  70

<210> SEQ ID NO 8
<211> LENGTH: 75
<212> TYPE: PRT
<213> ORGANISM: Homo sapiens

<400> SEQUENCE: 8

Glu Cys Leu Pro Cys Gly Glu Ser Glu Phe Leu Asp Thr Trp Asn Arg
 1               5                  10                  15

Glu Thr His Cys His Gln His Lys Tyr Cys Asp Pro Asn Leu Gly Leu
             20                  25                  30

Arg Val Gln Gln Lys Gly Thr Ser Glu Thr Asp Thr Ile Cys Thr Cys
         35                  40                  45
```

```
Glu Glu Gly Trp His Cys Thr Ser Glu Ala Cys Glu Ser Cys Val Leu
 50                  55                  60

His Arg Ser Cys Ser Pro Gly Phe Gly Val Lys
 65                  70                  75
```

<210> SEQ ID NO 9
<211> LENGTH: 34
<212> TYPE: PRT
<213> ORGANISM: Homo sapiens

<400> SEQUENCE: 9

```
Asp Cys Val Pro Cys Gln Glu Gly Lys Glu Tyr Thr Asp Lys Ala His
 1               5                  10                  15

Phe Ser Ser Lys Cys Arg Arg Cys Arg Leu Cys Asp Glu Gly His Gly
                20                  25                  30

Leu Glu
```

<210> SEQ ID NO 10
<211> LENGTH: 58
<212> TYPE: PRT
<213> ORGANISM: Homo sapiens

<400> SEQUENCE: 10

```
Cys Arg Pro Cys Gly Pro Gly Phe Tyr Asn Asp Val Val Ser Ser Lys
 1               5                  10                  15

Pro Cys Lys Pro Cys Thr Trp Cys Asn Leu Arg Ser Gly Ser Glu Arg
                20                  25                  30

Lys Gln Leu Cys Thr Ala Thr Gln Asp Thr Asp Thr Val Cys Arg Cys
            35                  40                  45

Arg Ala Gly Thr Gln Pro Leu Asp Ser Tyr
 50                  55
```

<210> SEQ ID NO 11
<211> LENGTH: 69
<212> TYPE: PRT
<213> ORGANISM: Homo sapiens

<400> SEQUENCE: 11

```
Cys Ser Pro Cys Pro Pro Asn Ser Phe Ser Ser Ala Gly Gly Gln Arg
 1               5                  10                  15

Thr Cys Asp Ile Cys Arg Gln Cys Lys Gly Val Phe Arg Thr Arg Lys
                20                  25                  30

Glu Cys Ser Ser Thr Ser Asn Ala Glu Cys Asp Cys Thr Pro Gly Phe
            35                  40                  45

His Cys Leu Gly Ala Gly Cys Ser Met Cys Glu Gln Asp Cys Lys Gln
     50                  55                  60

Gly Gln Glu Leu Thr
 65
```

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 12

```
Tyr Cys Glu Leu Ser Gln Tyr Leu Cys Tyr
 1               5                  10
```

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Novel Sequence

<400> SEQUENCE: 13

Tyr Cys Trp Ser Gln Asn Leu Cys Tyr
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Novel Sequence

<400> SEQUENCE: 14

Tyr Cys Trp Ser Gln Asn Tyr Cys Tyr
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Novel Sequence

<400> SEQUENCE: 15

Tyr Cys Trp Ser Gln Tyr Leu Cys Tyr
 1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Novel Sequence

<400> SEQUENCE: 16

Tyr Cys Phe Thr Ala Ser Glu Asn His Cys Tyr
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Novel Sequence

<400> SEQUENCE: 17

Tyr Cys Phe Thr Asn Ser Glu Asn His Cys Tyr
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Novel Sequence

```
<400> SEQUENCE: 18

Tyr Cys Phe Thr Arg Ser Glu Asn His Cys Tyr
 1               5                  10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 19

Phe Cys Ala Ser Glu Asn His Cys Tyr
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 20

Tyr Cys Ala Ser Glu Asn His Cys Tyr
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 21

Phe Cys Asn Ser Glu Asn His Cys Tyr
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 22

Phe Cys Asn Ser Glu Asn Arg Cys Tyr
 1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 23

Phe Cys Asn Ser Val Glu Asn Arg Cys Tyr
 1               5                  10

<210> SEQ ID NO 24
<211> LENGTH: 11
```

```
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 24

Tyr Cys Arg Lys Glu Leu Gly Gln Val Cys Tyr
  1               5                  10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 25

Tyr Cys Lys Glu Pro Gly Gln Cys Tyr
  1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 26

Tyr Cys Arg Lys Glu Met Gly Cys Tyr
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 27

Phe Cys Arg Lys Glu Met Gly Cys Tyr
  1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 28

Tyr Cys Ser Gln Ser Val Ser Asn Asp Cys Phe
  1               5                  10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Novel
      Sequence
```

-continued

```
<400> SEQUENCE: 29

Phe Cys Val Ser Asn Asp Arg Cys Tyr
1               5
```